US006558926B1

(12) United States Patent
Demain et al.

(10) Patent No.: US 6,558,926 B1
(45) Date of Patent: May 6, 2003

(54) METHOD FOR PRODUCTION OF TETANUS TOXIN USING MEDIA SUBSTANTIALLY FREE OF ANIMAL PRODUCTS

(75) Inventors: Arnold L. Demain, Wellesley, MA (US); Aiqi Fang, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/354,959

(22) Filed: Jul. 16, 1999

(51) Int. Cl.$^7$ ............................ C12P 21/04; C12N 1/20; C12N 1/00
(52) U.S. Cl. ................ 435/71.1; 435/252.7; 435/253.6; 435/842
(58) Field of Search ............................ 435/252.7, 71.1, 435/253.6, 842

(56) References Cited

FOREIGN PATENT DOCUMENTS

WO    WO 98/54296    * 12/1998

OTHER PUBLICATIONS

ATCC Catalogue. ATCC Bacteria and Bacteriophages. 19th edition. 1996., p. 479, 483.*
Demarchi t al. Analecta Veterinaria. Dec. 1970. vol. 2, No. 1–3, pp. 93–97.*
De Luca, et al., "Nitrogen–Gas Bubbling During the Cultivation of *Clostridium Tetani* Produces a Higher Yield of Tetanus Toxin for the Preparation of its Toxoid" *Microbiol. Immunol.* 41(2): 161–163, 1997.
Jagicza, et al., "Large–Scale Production of Tetanus Toxin in a Fermentor", *Ann. Immunol. Hung.,* 20–22: 189–196, 1983.
Maroczi, J. "Contribution of Toxin Production of *Clostridium Tetani* in Beef–Heart Broth Digested with Pepsin and Trypsin", *Ann. Immunol. Hung,* 10: 95–100, 1967.
Park, et al., "Comparative Investigation on the Medium for the Tetanus Toxin Production", Abstract.
Rappuoli, et al., "Toxin–Based Vaccines", *Handb. Exp. Pharmacol.* 133: 201–224, 1999.
Wirz, et al., "Tetanus Vaccine—Present Status." *Advances in Biotechnical Processes,* 13: 35–56, 1990.
"Model Programme for the Production of Vaccines in Developing Countries" *United Nations Industrial Development Organization* 86(61649):48–54, 1986.
"Tetanus Toxoid" Manual for the Production and Control of Vaccines 9–61.
Bilko, "Cultivation of Clostridia on Nutrient Media with Polyacrylamide Gel" *Microbiology Journal* 48:24–27, 1986.
Clifton, "The Utilizization of Amino Acids and Related Compounds by *Clostridium Tetani*" *J. Bacteriology* 44:179–183, 1943.
Edlich, et al., "Tetanus" *Comprehensive Therapy* 12(4):12–21, 1986.
Feeney, et al., "Growth Requirements of *Clostridium Tetani*" *J. Bacteriology* 46:559–562, 563–571, 1943.

Fraenkel–Conrat, et al., "The Reaction of Formaldehyde with Proteins. V. Cross–linking between Amino and Primary Amide or Guanidyl Groups" *J. Am. Chem. Soc.* 70:2673–2684, 1948.
Galazka, et al., "The Present Status of Tetanus and Tetanus Vaccination" *Clostridial Neurotoxins* 195:31–53, 1995.
Goldie, et al., "Titration of Tetanal Toxins, Toxoids and Antitoxins with the Flocculative Test" *J. Inf. Dis.* 71:212–219, 1942.
Knight, et al., "The Preparation and Properties of Immunopurified Tetanus Toxoid" *Proceedings of the Fourth International Conference on Tetanus* 775–786, Apr. 6–12, 1975.
Latham, et al., "Tetanus Toxin Production in the Absence of Protein" *Appl. Microbiol.* 10:146–152, 1962.
Lerner, et al., "The Fermentation of Glucose by *Clostridium Tetani*" *Arch. Biochem.* 8:183–196, 1945.
Middlebrook, et al., "Immunodiagnosis and Immunotherapy of Tetanus and Botulinium Neurotoxins" *Clostridial Neurotoxins* 195:89–122, 1995.
Moloney, et al., "Titration of Tetanal Toxins and Toxoids by Flocculation" *J. Immunol.* 48:345–354 (1944).
Mueller, et al., "Growth Requirements of *Clostridium Tetani*" *J. Bacteriology* 43:763–772, 1943.
Mueller, et al., "Variable Factors Influencing the Production of Tetanus Toxin" *J. Bacteriology* 67:271–277, 1954.
Mueller, et al., "Separation From Tryptic Digests of Casein of Some Acid–Labile Components Essential in Tetanus Toxin Formation" *J. Bacteriology.* 69:634–642, 1955.
Murray, et al., "Microbial Physiology and Structure" *Medical Microbiology,* The CV Mosby Company, St. Louis 189–193, 1990.
Ozutsumi, et al., "Rapid, Simplified Method for Production and Purification of Tetanus Toxin" *Applied and Environmental Microbiology* 49(4):939–943, 1985.
Pal, et al., "An ELISA For Quantitation of Tetanus Toxin" *Indian J. Med. Res.* 91:124–125, 1990.
Pillemer, "The Solubility and Precipitation of Tetanal Toxin and Toxoid in Methanol–Water Mixtures Under Controlled Conditions of pH, Ionic Strength and Temperature" *J. Immunol.* 53:237–250, 1946.
Relyveld, "Tetanus Toxin: A Model For Studies in Immunology" *Sixth International Conference on Tetanus,* Lyon, France 347–361, 1981.

(List continued on next page.)

Primary Examiner—Sandra E. Saucier
Assistant Examiner—Vera Afremova
(74) Attorney, Agent, or Firm—Choate, Hall & Stewart

(57) ABSTRACT

The present invention provides a system for the growth of *C. tetani* and production of Tetanus Toxin for use in formulating Tetanus Toxoid preparations. The system includes growth media that contain significantly reduced levels of meat or dairy by-products using non-animal based products to replace the animal-derived products. Preferred media are substantially free of animal-derived products.

21 Claims, 14 Drawing Sheets

OTHER PUBLICATIONS

Robb, L.A., "The Preparation of an Improved Tetanus Toxoid by Removal of an Sensitizing Fraction" *Proceedings of the Fourth International Conference on Tetanus* 735–743, Apr. 6–12, 1975.

Shone, et al., "Growth of Clostridia and Preparation on Their Neurotoxins" *Clostridial Neurotoxins* ed. Montecusso. Springer, 1995 143–160.

Stainer, D.W., "Problems in the Large-Scale Production of Tetanus Toxin" *Proceedings of the Fourth International Conference on Tetanus* 745–754, Apr. 6–12, 1975.

Stone, "A Modified Mueller Medium Without Native Protein for Tetanus Toxin Production" *Appl. Microbiol.* 1:166–168, 1953.

Stone, et al., "Effect of the Elimination of Native Proteins on the Yield and Purification Capacity of Tetanus Toxoid" *Applied Microbiol.* 2:262–263, 1954.

Thomson, R.O. "A Semi-Continuous Method for the Large-Scale Production of Tetanus Toxin" *Nature* 180:1126–1127, 1957.

Tsunashima, et al., "Excess Supplementation of Certain Amino Acids to Medium and Its Inhibitory Effect on Toxin Production by *Clostridium Tetani*" *Biken Journal* 7:161–163, 1964.

Van Hemert, et al., "Instructions for the Preparation of Bacterial and Viral Vaccines" *Rijks Instituut Voor de Volksgezondheid* 601–615, Jun., 1976.

Volkova, "Effect of the Medium Composition and pH Value on Sporulation of *Clostridium tetani*" Mikrobiol. Zn (MY8) Jul.–Aug., 48:24–27, 1986 (in Russian).

Wassilak, et al., Tetanus Toxoid: In: Plotkin SA, Mortimer, EA, eds. Vaccines. Philadelphia: Saunders. 57–90, 1994.

* cited by examiner

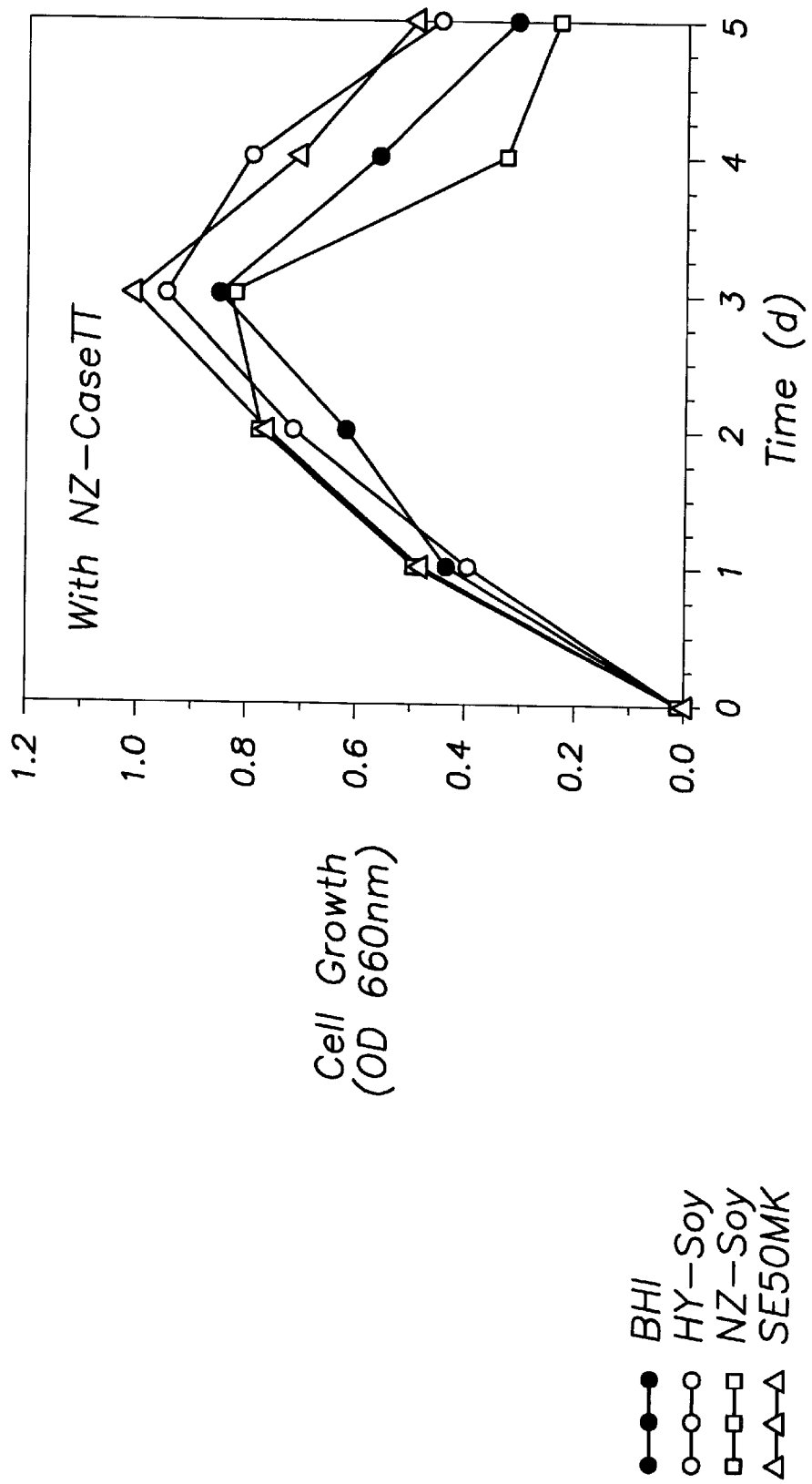
FIG.9-A

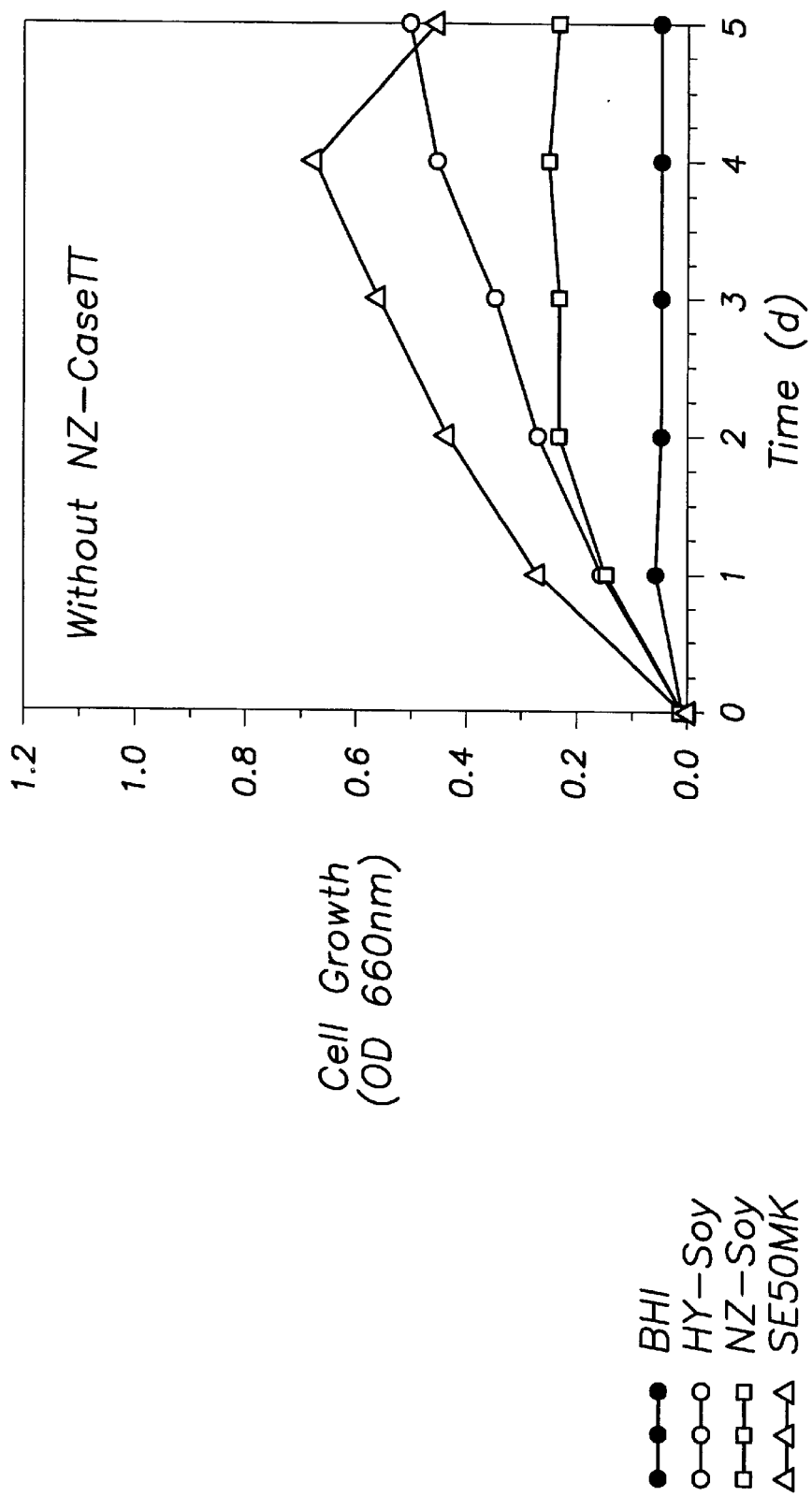
FIG.9-B

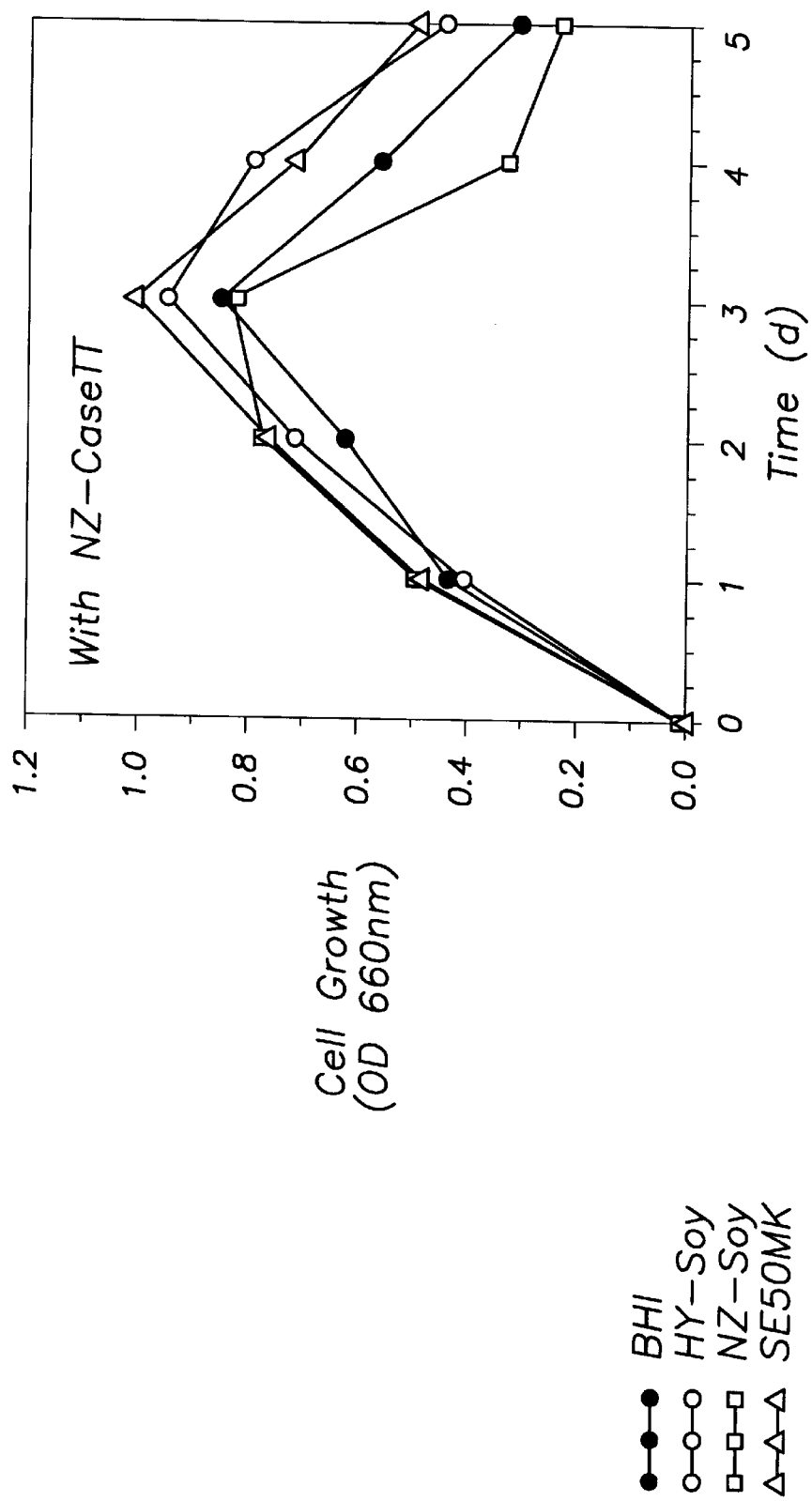
FIG.10-A

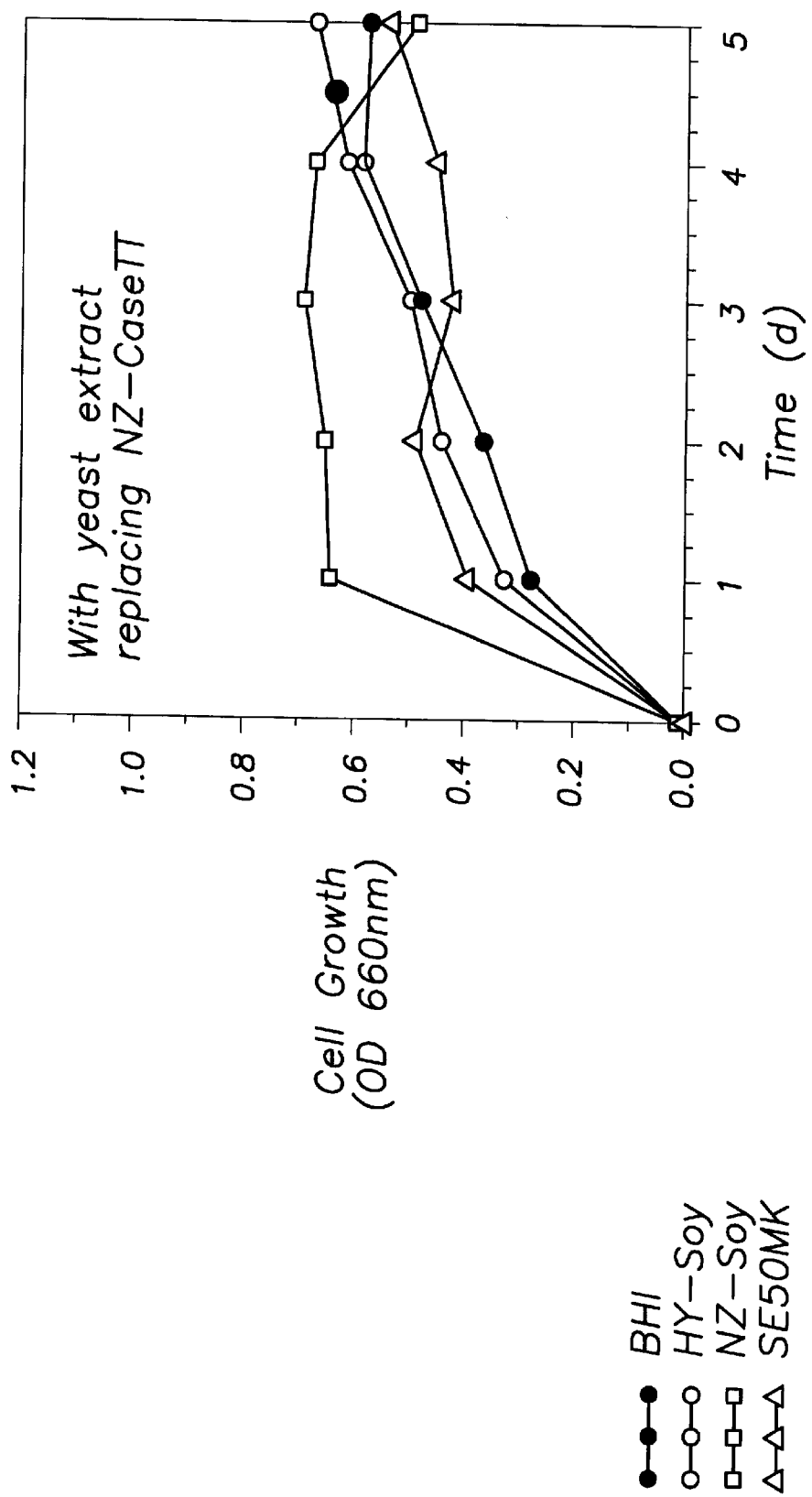
FIG. 10-B

METHOD FOR PRODUCTION OF TETANUS TOXIN USING MEDIA SUBSTANTIALLY FREE OF ANIMAL PRODUCTS

BACKGROUND

Tetanus is a life-threatening disease caused by infection with *Clostridium tetani* (*C. tetani*), a ubiquitous anaerobic spore-forming soil microbe. *C. tetani* causes disease by releasing a peptide toxin, Tetanus Toxin, that enters the nerve cells of the infected host and blocks release of neurotransmitters at inhibitory synapses. This blockage produces unregulated excitation of certain host neurons, resulting in uncontrollable muscle contraction and paralysis, typically of facial and back muscles. As recently as 1989, 10–40% of *C. tetani* infections of non-immunized hosts resulted in death.

For the past 50 years, widespread immunization programs have been in effect to protect against the effects of *C. tetani* infection. Vaccines are prepared from Tetanus Toxin that has been inactivated, usually by exposure to formalin (Descomby, *Can. Roy. Soc. Biol.* 91:239, 1924; Plotkin et al., *Vaccines*, 2nd. Edition, W. B. Saunders, 1994). The inactivated Toxin is known as Tetanus Toxoid.

The *C. tetani* vaccination effort, although it has achieved significant success, has been hampered by certain complications associated with preparation of the Tetanus Toxoid. Because Tetanus Toxin is an extremely potent and dangerous compound (the estimated lethal dose for a human is only 2.5 ng/Kg), it is necessary to inactivate the Toxin very early in its purification process so that the risks of exposure to even partially purified active Toxin is minimized. As mentioned above, Tetanus Toxin is usually inactivated by exposure to formalin, which destroys the activity of the peptide toxin by generating inter-peptide cross-links and adducts. Unfortunately, formalin reactivity is not specific to Tetanus Toxin. A large number of other microbial and media proteins are also cross-linked by formalin. Because the Tetanus Toxin must be treated with formalin at an early stage in its purification, the treatment produces a complex, heterogenous composition containing not only formalin-inactivated Tetanus Toxin, but also formalin adducts of other peptides and proteins that were present in the formalin-treated mixture.

Tetanus Toxin is usually prepared from *C. tetani* cells that have been grown in media containing animal and dairy by-products (e.g., casein digests, meat extracts) as sources of the proteins, peptides, and amino acids that are required for growth or that stimulate growth. Tetanus Toxoid preparations generated from such cells necessarily contain some amount of formalin adducts of animal proteins. A possible consequence of this fact is that some Toxoid preparations could contain carry-over amounts of undesirable contaminants, such as the protein agent (prion) that causes Bovine Spongioform Encephalopathy (BSE), or antigenic peptides that stimulate undesired immune reactions (e.g., anaphylactic reactions) in immunized subjects.

The medium used to grow *C. tetani* for Tetanus Toxoid preparation has a variety of additional problems as well. The standard medium, known as "MM", was developed in 1954 by Mueller and Miller (*J. Bacteriol.* 67:271, 1954) and contains glucose, beef heart infusion (BHI), NZ-Case or NZ-Case TT (an enzymatic digest of casein), some amino acids and vitamins, uracil, and inorganic salts. The BHI component has proven to be particularly problematic, both because of the risk that it will contain undesirable products that may be carried over into the final Toxoid preparation (see, for example, Robb, *Proc. 4th Internat. Conf. Tetanus.*, Dankar, Senegal, pp. 735–43, 1975) and because of its variability from lot to lot.

The NZ Case component of MM medium has also caused problems due to its variability (see, for example, Stainer, *Proc. 4th Internat. Conf Tetanus.*, Dakar, Senegal, pp. 745–54, 1975). It is now common practice for producers of Tetanus Toxoid preparations to screen numerous lots of NZ Case to identify a particular lot that results in high level Tetanus Toxin production. Once such a lot is identified, the Toxoid producer will typically purchase the entire lot.

Yet another problem with the MM medium typically used to culture *C. tetani* for Tetanus Toxoid preparation is that the medium has proven to be very sensitive to "cooking," in a manner that is independent of the requirement for sterilization. Apparently, extended cooking protocols can produce Maillard adducts and/or can degrade medium components such as proteins and peptides, so that a less effective growth medium is produced when a particular batch of medium is imperfectly cooked.

Finally, the process of *C. tetani* fermentation in MM medium generates $H_2S$, which is toxic to *C. tetani*, and may also generate some alcohols that can similarly be toxic. *C. tetani* growth in this medium, not to mention Toxin production, can be dramatically affected by the rate at which the head space in a fermenter is purged or gas exchanged, creating yet another point at which the extent and quality of Toxoid preparation can vary significantly from one batch to another.

There is a need for the development of an improved system for preparing Tetanus Toxoid that minimizes these risks and problems. Preferably, the system should allow for reproducible, high levels of Toxin production, and should minimize the dangers associated with formation of animal- or dairy-product adducts. There is a particular need for the development of a *C. tetani* culture medium and growth protocol that does not utilize meat or dairy by-products.

SUMMARY OF THE INVENTION

The present invention provides a system for the growth of *C. tetani* and production of Tetanus Toxin for use in formulating Tetanus Toxoid preparations. The inventive system allows production of high levels of Tetanus Toxin and preferably utilizes at least one growth medium that contains significantly reduced levels of meat or dairy by-products as compared with MM medium; preferred media embodiments are substantially free of such components.

In one aspect, the present invention provides media that contain reduced levels of animal or dairy byproducts and are preferably substantially free of animal or dairy byproducts. For the purpose of the present invention, animal or dairy byproducts means any compound or collection of compounds that was produced in or by an animal cell, whether in a living organism or in vitro. Preferred non-animal sources of media ingredients such as proteins, amino acids, and nitrogen, include but are not limited to vegetables, microbes (such as yeast) and synthetic compounds.

In another aspect, the present invention provides methods of preparing Tetanus Toxin using at least one medium that is substantially free of animal or dairy byproducts. In one embodiment, Tetanus Toxin is produced by culturing an organism of the genus Clostridium in a fermentation medium substantially free of animal products.

In another embodiment of the present invention, Tetanus Toxin is produced by culturing an organism of the genus Clostridium in a fermentation medium substantially free of animal products and containing vegetable-derived products.

In yet another embodiment, Tetanus Toxin is produced by culturing an organism of the genus Clostridium in a fermentation medium substantially free of animal products and containing soy-based products.

In yet another preferred embodiment, Tetanus Toxin is produced by culturing *Clostridium tetani* in a fermentation medium substantially free of animal products and containing hydrolyzed soy as a substitute for animal-derived products. Preferably, growth in a fermentation medium proceeds until at least cell lysis occurs. The source of *C. tetani* used for inoculation of the fermentation medium may be obtained from a seed medium containing *C. tetani*. Preferably, *C. tetani* grown in a seed medium and used as an inoculant for a fermentation medium has not undergone cell lysis. The source of *C. tetani* used for inoculation of the seed medium may be obtained from a lyophilized culture. *C. tetani* may be lyophilized as a culture in animal milk or soy milk. Preferably *C. tetani* is lyophilized as a culture in soy milk.

The present invention also provides a composition comprising a medium substantially free of animal-derived products for culturing an organism and also comprising an organism of the genus Clostridium.

In one embodiment, the composition comprises a medium substantially free of animal-derived products while containing at least one product derived from a non-animal source, and also comprising an organism of the genus Clostridium.

In another embodiment, the composition comprises a medium substantially free of animal-derived products while containing at least one product derived from a vegetable, and also comprising an organism of the genus Clostridium.

In yet another embodiment, the composition comprises a medium substantially free of animal-derived products while containing at least one product derived from soybeans, and also comprising an organism of the genus Clostridium.

DESCRIPTION OF THE DRAWINGS

FIGS. 9(A. and B.) show the effect on cell growth of NZ-CaseTT removal from various media employing BHI or soy peptones.

FIGS. 10(A. and B.) depict the effect on cell growth of replacing NZ-CaseTT with yeast extract in media containing either BHI or a soy product.

DETAILED DESCRIPTION OF CERTAIN PREFERRED EMBODIMENTS OF THE INVENTION

Figure 1:
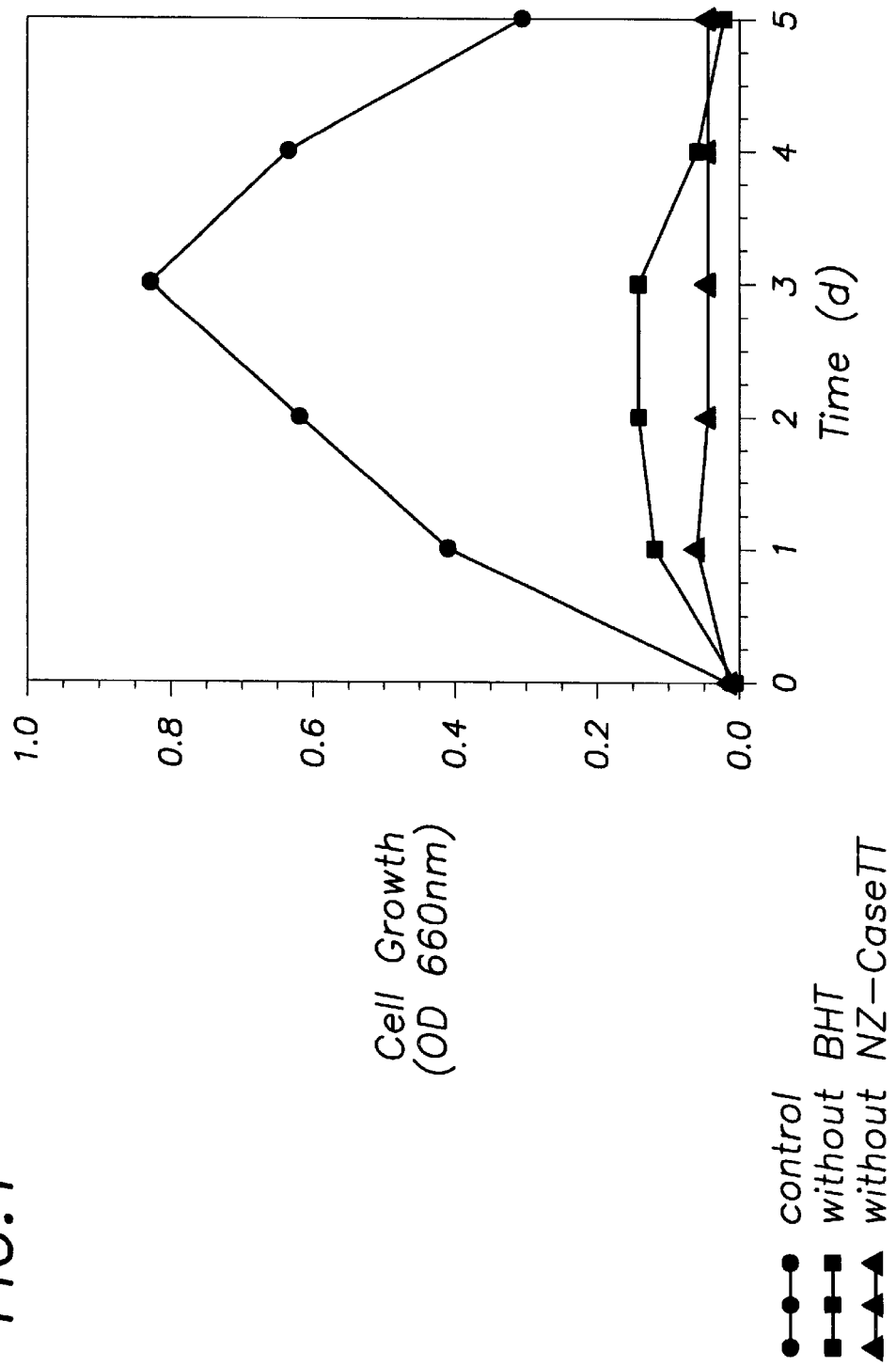
FIG. 1 presents a graphical representation of the requirement for BHI and NZ-CaseTT for *C. tetani* growth in control fermentation medium.

The present invention provides a system for the growth of the microorganism *C. tetani*, and production of Tetanus Toxin by *C. tetani* for use in formulating Tetanus Toxoid preparations. The system includes growth media that contain significantly reduced levels of meat or dairy by-products; preferred media embodiments are substantially free of such components. Alternatively or additionally, the growth media lack one or more components found in MM medium. Preferably, the media lack one or both of BHI and NZ-Case.

The present invention encompasses the finding that animal-based products are not required in media for growth of *C. tetani*, and particularly that vegetable-based products can replace animal-based products typically employed in such media for the growth of *C. tetani*.

Currently, standard media that are commonly used for growth and production of products of fermentation by microorganisms contain ingredients derived from animals. One such growth medium is MM (Mueller and Miller. *J. Bacteriol.* 67:271, 1954). Animal components in MM include beef heart infusion (BHI), and NZ-CaseTT (hydrolyzed casein, a protein found in animal milk). Replacing the animal components of growth media with vegetable-based products reduces the potential for contamination by biological molecules such as proteins and viruses that exist in animals. By way of example and not limitation, these molecules include the protein agent that causes Bovine Spongioform Encephalopathy (commonly known as "Mad Cow's disease"), antigenic peptides that stimulate undesired immune reactions in immunized subjects (e.g., anaphylactic reactions), and virally-contaminated animal products.

In accordance with the present invention, preferred media for growth of *C. tetani* contain animal-derived ingredients comprising no more than 5–10% of the total weight of the media. More preferably, the growth media are completely free of animal-derived products. Most preferably, all media and cultures used for the growth of *C. tetani* for the production of Tetanus Toxin are completely free of animal-derived products. These media include but are not limited to media for small and large scale fermentation of *C. tetani*, media for growth of cultures of *C. tetani* used to inoculate the fermentation media (i.e. seed media), and media used for long-term storage of cultures of *C. tetani* (e.g. stock cultures).

In certain preferred embodiments of the present invention, the media for the growth of *C. tetani* and production of Tetanus Toxin contain soy-based products that replace animal by-products. Preferably, these media include soybean by-products that are hydrolyzed and that are soluble in water. However, insoluble soy products can also be used in the present invention to replace animal products. Common animal by-products which can be substituted by soy products include, but are not limited to, beef heart infusion (BHI), hydrolyzed caseins, peptones, and dairy by-products such as animal milk.

It is preferable that media containing soy-based products for the growth of C. tetani be similar to commonly used growth media containing animal derived products (e.g MM) except that substantially all animal-derived products are replaced with vegetable-derived products. Ingredients in MM such as Ca-pantothenate, uracil, thiamine, riboflavin, pyridoxine, and biotin are not essential for maximum growth of C. tetani in media containing soy-based products, but can be included in growth media. By way of example and not limitation, soy-based fermentation media can comprise a soy-based product, a source of carbon such as glucose, salts such as NaCl and KCl, phosphate-containing ingredients such as $Na_2HPO_4$, $KH_2PO_4$, divalent cations such as iron and magnesium, iron powder, and amino acids such as L-cysteine and L-tyrosine. Media used to grow cultures of C. tetani for inoculation (i.e. seed medium) of the fermentation media preferably contain at least a soy-based product, a source of salt such as NaCl, and a carbon source such as glucose.

The present invention provides a method for the growth of C. tetani that maximizes the production of Tetanus Toxin using media that are substantially free of animal-derived products. It is important to note that growth of C. tetani and production of Tetanus Toxin by C. tetani are not always directly correlated. Several factors including time of cell lysis and maximum levels of growth can influence the levels of toxin production. Growth for production of C. tetani and Tetanus Toxin proceeds by fermentation in media containing soy by-products that replace ingredients derived from animal by-products. The inoculant for the fermentation medium can be derived from a smaller scaled growth medium defined in the present application as a seed medium. Depending on the size and volume of the fermentation step, the number of successive growths in seed media to increase the biomass of the culture can vary. To grow a suitable amount of C. tetani for inoculating the fermentation medium, one step or multiple steps involving growth in a seed medium can be performed. For a method of growing C. tetani that is free of animal-derived products, it is preferable that growth of C. tetani originates from a culture stored in non-animal derived media. The stored culture, preferably lyophilized, is produced by growth in media containing proteins derived from soy and lacking animal by-products. It is recognized that growth of C. tetani in a fermentation medium may proceed by inoculation directly from a stored, lyophilized culture.

In a preferred embodiment of the present invention, growth of C. tetani proceeds in two phases—seed growth and fermentation—both of which are carried out in anaerobic environments. The seed growth phase is generally used to "scale-up" the quantity of the microorganism from a stored culture. The purpose of the seed growth phase(s) is to increase the quantity of the microorganism available for fermentation. In addition, the seed growth phase allows relatively dormant microbes in stored cultures to rejuvenate and grow into actively growing cultures. Furthermore, the volume and quantity of viable microorganisms used to inoculate the fermentation culture can be controlled more accurately from an actively growing culture than from a stored culture. Thus, growth of a seed culture for inoculation of the fermentation medium is preferred. In addition, any number of consecutive steps involving growth in seed media to scale-up the quantity of C. tetani for inoculation of the fermentation medium can be used. It is noted that growth of C. tetani in the fermentation phase can proceed directly from the stored culture by direct inoculation.

In the fermentation phase, a portion of a seed medium or all of a seed medium containing C. tetani from the seed growth is used to inoculate a fermentation medium. Preferably, approximately 2–4% of a seed medium having C. tetani from the seed growth phase is used to inoculate the fermentation medium. Fermentation is used to produce the maximum amount of microbe in a large-scale anaerobic environment (Ljungdahl and Wiegel. *Manual of industrial microbiology and biotechnology*. 1986. ed. Demain and Solomon. American Society for Microbiology, Washington, D.C. p. 84).

Tetanus Toxin may be isolated and purified using methods of protein purification well known to those of ordinary skill in the protein purification art (Coligan et al. "Current Protocols in Protein Science." Wiley & Sons; Ozutsumi et al. Appl. Environ. Microbiol. 49:939–943. 1985. Both citations are incorporated herein in their entirety).

Seed Medium

Preferably for production of Tetanus Toxin, cultures of C. tetani are grown in a seed medium for inoculation of the fermentation medium. The number of successive steps involving growth in a seed medium can vary depending on the scale of the production of Tetanus Toxin in the fermentation phase. However, as previously discussed, growth in the fermentation phase may proceed directly from inoculation from a stored culture. Animal-based seed media generally are comprised of BHI, bacto-peptone, NaCl, and glucose for growth of C. tetani. As previously discussed, alternative seed media may be prepared in accordance with the present invention in which animal-based components are substituted with non-animal-based components. For example but without limitation, soy-based products can substitute for BHI and bacto-peptone in the seed medium for growth of C. tetani and production of Tetanus Toxin. Preferably, the soy-based product is soluble in water and comprises hydrolyzed soy, although cultures of C. tetani can grow in media containing insoluble soy. However, levels of growth and subsequent toxin production are greater in media derived from soluble soy products.

Any source of soy-based products may be used in accordance with the present invention. Preferably, the soy is hydrolyzed soy. Sources of hydrolyzed soy are available from a variety of commercial vendors. These include but are not limited to Hy-Soy (Quest International), Soy peptone (Gibco) Bac-soytone (Difco), AMISOY (Quest), NZ soy (Quest), NZ soy BL4, NZ soy BL7, SE50M (DMV International Nutritionals, Fraser, N.Y.), and SE50MK (DMV). Most preferably, the source of hydrolyzed soy is Hy-Soy or SE50MK. Other sources of hydrolyzed soy have been tested and can be found in Tables 9–12.

Concentrations of Hy-Soy in the seed medium in accordance with the present invention range between 25–200 g/L. Preferably, the concentration of Hy-Soy in the seed medium ranges between 50–150 g/L. Most preferably the concentration of Hy-Soy in the seed medium is approximately 100 g/L. In addition, the concentration of NaCl ranges between 0.1–2.0 g/L. Preferably the concentration of NaCl ranges between 0.2–1.0 g/L. Most preferably, the concentration of NaCl in the seed medium is approximately 0.5 g/L. The concentration of glucose ranges between 0.1 g/L and 5.0 g/L. Preferably, the concentration of glucose ranges between 0.5–2.0 g/L. Most preferably, the concentration of glucose in the seed medium is approximately 1.0 g/L. It is also preferred but not necessary for the present invention that the glucose is sterilized by autoclaving together with the other components of the seed medium. The preferred pH level of the seed medium prior to growth ranges between 7.5–8.5. Most preferably, the pH of the seed medium prior to growth of C. tetani is approximately 8.1.

Growth of C. tetani in the seed medium may proceed in one or more stages. Preferably, growth in the seed medium proceeds in two stages. In stage one, a culture of C. tetani is suspended in a quantity of seed medium and incubated at 34±1° C. for 24–48 hours in an anaerobic environment. Preferably, growth in stage one proceeds for approximately 48 hours. In stage two, a portion or all of the stage one medium containing C. tetani is used to inoculate a stage two seed medium for further growth. After inoculation, the stage two medium is incubated at 34±1° C. for approximately 1–4 days also in an anaerobic environment. Preferably, growth in the stage two seed medium proceeds for approximately 3 days. It is also preferable that growth in seed media in any stage does not result in cell lysis before inoculation of fermentation media with the final growth in seed medium.

Fermentation Medium

Standard fermentation media containing animal by-products for the growth of C. tetani are based on a recipe of Mueller and Miller (MM; J. Bacteriol. 67:271, 1954). The ingredients in MM media containing animal by-products include BHI and NZ-CaseTT. NZ-CaseTT is a commercially available source of peptides and amino acids which are derived from the enzymatic digestion of caseins, a group of proteins found in animal milk. The present invention demonstrates that non-animal based products may be substituted for BHI and NZ-CaseTT in fermentation media. For example but without limitation, soy-based products can replace the animal-based components of MM media used for fermentation of C. tetani. Preferably, the soy-based products are water-soluble and derived from hydrolyzed soy, although as previously discussed, insoluble soy products can also be used to practice the present invention.

Any source of soy-based products may be used in accordance with the present invention. Preferably, the hydrolyzed soy is obtained from Quest International (Sheffield) under the tradename, Hy-Soy or from DMV International Nutritionals (Fraser, N.Y.) under the tradename, SE50MK. Soluble soy products can be also obtained from a variety of sources including but not limited to Soy peptone (Gibco) Bac-soytone (Difco), AMISOY (Quest), NZ soy (Quest), NZ soy BL4, NZ soy BL7, and SE50MK (DMV International Nutritionals, Fraser, N.Y.).

In another preferred embodiment of the present invention, the medium used for fermentation of C. tetani is free of animal by-products and comprises hydrolyzed soy, glucose, NaCl, $Na_2HPO_4$, $MgSO_4 7H_2O$, $KH_2PO_4$, L-cysteine, L-tyrosine, and powdered iron. As described for the seed medium, hydrolyzed soy can replace animal by-products in fermentation medium. These animal by-products include BHI and NZ-Case TT (enzymatically digested casein).

The concentration of Hy-Soy in the fermentation medium for production of Tetanus Toxin preferably ranges between approximately 10–100 g/L. Preferably, the concentration of Hy-Soy ranges between approximately 20–60 g/L. Most preferably, the concentration of Hy-Soy in the fermentation medium is approximately 35 g/L. For maximal production of Tetanus Toxin, particularly preferred concentrations of components in the fermentation medium are approximately 7.5 g/L, glucose; 5.0 g/L NaCl; 0.5 g/L $Na_2HPO_4$; 175 mg/L $KH_2PO_4$; 50 mg/L $MgSO_4$ $7H_2O$; 125 mg/L L-cysteine; and 125 mg/L L-tyrosine. The amount of powdered iron used can range from 50 mg/L to 2000 mg/L. Preferably, the amount of powdered iron ranges between approximately 100 mg/L and 1000 mg/L. Most preferably, the amount of powdered iron used in fermentation media ranges between approximately 200 mg/L and 600 mg/L.

For optimal levels of toxin production, the initial pH (before autoclaving) of the soy-based fermentation media ranges preferably between approximately 5.5 to 7.1. Preferably the initial pH of the fermentation medium is between approximately 6.0 to 6.2. As described for the seed medium, the components of the fermentation medium, including glucose and iron, are preferably autoclaved together for sterilization.

Preferably, a portion of the second stage seed medium used for growth of C. tetani is used to inoculate the fermentation medium. Fermentation occurs in an anaerobic chamber at approximately 34±1° C. for approximately 7 to 9 days. Growth is monitored by measuring the optical density (O.D.) of the medium. Fermentation preferably is stopped after cell lysis has proceeded for at least 48 hours as determined by growth measurement (optical density). As cells lyse, the O.D. of the medium will decrease.

Preservation Medium

In a preferred embodiment of the present invention, cultures of C. tetani used for long-term storage of C. tetani and inoculation of the seed medium are grown and lyophilized in soy-milk prior to storage at 4° C. Cultures of C. tetani in animal milk lyophilized for storage can also be used for the production of Tetanus Toxin. However, to maintain media that are substantially free of animal by-products throughout the production of Tetanus Toxin, it is preferred that the initial culture of C. tetani be preserved in soy milk and not animal milk.

Example 17 shows the results of experiments designed to examine the growth of C. tetani and the production of Tetanus Toxin in soy-based fermentation media using cultures of C. tetani lyophilized in animal-milk versus soy-milk as an inoculant. The results show that growth of C. tetani and production of Tetanus Toxin with lyophilized cultures of C. tetani in soy-milk is comparable to growth and production from cultures stored in animal milk.

Experimental Results

The ingredients of the MM medium containing animal-based products are shown in Table 5. Experiments were performed to test the ability of soy products to replace BHI for growth in fermentation media such as MM medium. The results of these experiments are summarized in Examples 3–4, Tables 8–10 and FIGS. 2–8. These results indicate that soy-based products can replace BHI for growth of C. tetani. Of the sources of soy tested, Hy-Soy and SE50MK were the best replacements for BHI for growth of C. tetani as measured by optical density. However, growth of C. tetani and production of Tetanus Toxin are not always directly correlated.

Table 11 indicates that the highest levels of toxin produced resulted from media containing 23 g/L of Hy-Soy. However, as indicated in Table 10, maximum growth of C. tetani was produced in a medium containing 34 g/L of Hy-Soy at day 3 or in a medium containing 34 g/L of SE50MK at day 3. Therefore, as a replacement for BHI in growth media, Hy-Soy is preferred for production of Tetanus Toxin (Table 11), even though use of SE50MK results in greater growth of C. tetani as compared to Hy-Soy (Table 10). However, use of SE50MK as a source of soy may be utilized in the present invention. It is important to note without being limited by theory that maximum growth of *C. tetani* does not directly correlate with maximum production of Tetanus Toxin due to several factors including the relationship between growth and cell lysis.

Experiments described in Example 6–8 were conducted to test the ability of non-animal derived products to replace NZ-CaseTT in fermentation media for growth of C tetani. Table 13 in Example 6 shows that soy products can replace BHI and NZ-CaseTT for growth of *C. tetani*. Table 14 and FIG. 10 show that a yeast extract can partially replace NZ-CaseTT in media for growth of *C. tetani*, but that corn steep, and Proflo, a yellow flour made from cottonseed (Traders Protein; Memphis, Tenn.) cannot be used to replace NZ-CaseTT in a fermentation medium. Table 15 and 16 summarize experiments examining the ability of yeast and malt extracts to enhance growth and toxin production by *C. tetani*. Table 15 indicates that growth of *C. tetani* in media with Hy-Soy replacing BHI and NZ-CaseTT is enhanced by the addition of a yeast extract (see day 4 Hy-Soy only versus day 6 Hy-Soy plus yeast extract from Difco). However, yeast extracts did not improve the production of Tetanus Toxin in media containing Hy-Soy (Table 16).

Table 17 shows that yeast extracts except Hy-Yest 412 can partially replace NZ-CaseTT for growth. However, as indicated in Table 18 no yeast extract can replace NZ-CaseTT for toxin production. Malt extract had no ability to replace NZ-CaseTT. In addition, Hy-Soy without yeast extract is fully capable of substituting for animal by-products in media for toxin production. Therefore, it appears that the use of yeast extracts in growth media inhibits the production of toxin when used to substitute for NZ-CaseTT in the presence of Hy-Soy.

Experiments on the optimal concentration of Hy-Soy in media for growth of *C. tetani* show that concentrations of Hy-Soy greater than approximately 23 g/L can fully replace BHI and NZ-CaseTT for fermentation of *C. tetani* and toxin production (Table 19–20). More specifically, these results show that approximately 57 g/L of Hy-Soy in fermentation media is optimal for growth but that approximately 34 g/L of Hy-Soy results in maximum toxin production. However, the results should be interpreted with caution due to the fact that cells from growth on media with 46 g/L and 57 g/L of Hy-Soy had not lysed by the end of the experiment.

Experiments summarized in Table 23 were designed to examine the ability of Hy-Soy to replace BHI and NZ-CaseTT in seed media. These results demonstrate that Hy-Soy or Hy-Soy plus Hy-Yest can replace BHI and bacto-peptone in seed growth. Preferably, the seed medium utilizes approximately 100 g/L of Hy-Soy as a nitrogen source replacing animal by-products. Table 24 summarizes experiments examining the growth of *C. tetani* in fermentation media containing Hy-Soy, Hy-Soy plus NZ-Case TT, or BHI plus NZ-Case TT. The three fermentation media listed were each inoculated with four different seed media (A-D; Table 22). The data in Table 23 and 24 indicate that growth of *C. tetani* in seed media and fermentation media with Hy-Soy replacing BHI and NZ-CaseTT is comparable to growth in media with BHI and NZ-CaseTT.

Furthermore, the data in Table 25 indicate that toxin production by *C. tetani* grown in seed medium and fermentation medium containing Hy-Soy as a replacement for BHI and NZ-CaseTT reached (or exceeded) levels attained in media containing BHI and NZ-CaseTT. For a comparison, see Fermentation nitrogen source: Hy-Soy only; row B and C; day 9 (Lftoxin=57.5) versus Fermentation nitrogen source NZ-CaseTT plus BHI row A-D (Lf toxin=42.5).

Additional experiments were performed to examine the effects of varying the concentration of Hy-Soy and Hy-Yest in seed media on growth and toxin production. Tables 26–27 summarize data on the growth of *C. tetani* in seed media with different concentrations of Hy-Soy (B and C) or HySoy plus Hy Yest (D). Tables 26–27 demonstrate that Hy-Soy can replace BHI and bacto-peptone as the source of nitrogen in the seed medium and that Hy-Soy is a better source of nitrogen than [HySoy+Hy Yest] in seed medium for subsequent toxin production. Moreover, Tables 26–34 show that of the concentrations of Hy-Soy tested, 100 g/L of HySoy in a seed medium with subsequent inoculation of a fermentation medium results in the highest levels of Tetanus Toxin produced. Preferably, the concentration of Hy-Soy in the seed medium for optimal production of Tetanus Toxin is between approximately 25–200 g/L. More preferably, the concentration of Hy-Soy in the seed medium for optimal production of Tetanus Toxin is between approximately 25–200 g/L. Preferably, the first stage of growth in the seed medium proceeds for approximately 48 hours.

Experiments summarized in Example 12 (Tables 32–34) were designed to determine the optimum percentage of the second stage seed growth of *C. tetani* for inoculating a fermentation medium. In addition, these experiments examined the effects of varying the period of growth for the second stage seed on the production of toxin in the fermentation step. The results show that using *C. tetani* grown in the second stage seed medium for 14 days is suitable for growth and toxin production. After 4 days, the cells appear to lyse. Preferably, the second stage seed medium containing *C. tetani* is incubated for growth for approximately 3 days. Use of 2–4% of the second stage seed medium containing *C. tetani* grown for 3 days as an inoculum for full scale fermention appears to be optimal and preferred for Tetanus Toxin production.

The results of Tables 35–38 indicate that the concentration of powdered iron is a factor affecting toxin production when the powdered iron is autoclaved with other components in the medium for sterilization. The data (Tables 51–53) show that the medium labeled MC1 containing 0.25 g of iron per L of the control medium autoclaved together with the medium resulted in the highest levels of Tetanus Toxin production. This medium differs from control medium (labeled MC2) only by the amount of powdered iron (0.25 g vs 0.50 g). The concentration of powdered iron is a factor affecting toxin production when the powdered iron was autoclaved with other components in the medium. Medium containing 0.25 g/L of powdered iron produced the highest levels of toxin, and medium containing 2.0 g/L of powdered iron produced the lowest levels. Iron concentration did not appear to affect the levels of toxin production when the iron was autoclaved separately from the rest of the media.

Example 14 describes experiments designed to study the effect of different methods of media sterilization in the seed medium on the production of toxin by *C. tetani* in the fermentation medium. The results show that *C. tetani* grows faster in seed medium containing glucose that was autoclaved with the other components of the seed medium when compared to media containing filter-sterilized glucose or glucose autoclaved separately. Tetanus Toxin production was slightly higher in fermentation medium when glucose was autoclaved with the other fermentation medium components than when glucose was autoclaved separately or filtered separately. Thus, autoclaving glucose with the rest of the medium is somewhat beneficial for toxin production in fermentation medium.

Tables 41–42 in Example 15 show that the components of the Mueller and Miller medium not present in our Hy-Soy medium when added to medium containing Hy-Soy as the major source of nitrogen do not markedly improve growth or toxin production in the Hy-Soy fermentation medium. The best production was observed with Hy-Soy seed in combination with Hy-Soy fermentation medium.

The experiment in Example 16 demonstrates that 0.5 g/L of powdered iron in the fermentation medium combined with the use of approximately 2% of the second stage seed culture as an inoculum is preferred for the production of Tetanus Toxin. Toxin production is low in medium without an iron source. In addition, sources of iron such as ferrous sulfate, ferrous gluconate, ferric citrate and ferric nitrate are not able to replace powdered iron for optimal production of toxin. However, growth of *C. tetani* and toxin production was observed when ferric citrate is used as the source of iron. Since previous experiments demonstrated that 0.25 g/L of powdered iron in fermentation media results in a high level of Tetanus Toxin produced, the amount of powdered iron in fermentation media for optimal production of Tetanus Toxin can range between approximately 0.25 g/L to approximately 0.50 g/L.

The following examples are meant to illustrated the preferred method of practicing the present invention. However, it is known by one of ordinary skill in the art that variations, modifications and adaptations to the present invention can provide similar results. It is expressly understood that such variations, modifications, and adaptations are within the scope of the present invention.

EXAMPLES

Materials and Methods

Microorganism

A lyophilized culture of *C. tetani* (preparation 3-ABI-13; prepared with cow's milk), stored at 4° C., was obtained from Wyeth-Lederle Vaccine and Pediatrics (Pearl River, N.Y.). A lyophilized culture of *C. tetani* (preparation SM-409-0998-1; prepared with soy milk), stored at 4° C., was obtained from Wyeth-Lederle Vaccine and Pediatrics (Pearl River, N.Y.).

All experiments and media were prepared with doubly-distilled water.

Seeding

SEED MEDIUM COMPOSITION: Seed medium was prepared from the following components (per 100 ml of medium):

TABLE 1

| NaCl | 0.5 g |
|---|---|
| Bacto-peptone | 1.0 g |
| Glucose | 1.0 g |
| BHI | to 100.0 ml |
| pH | 8.1 |
| (adjusted with 5 N NaOH) | |

SEED CULTURE: Lyophilized culture was suspended in 1 ml seed medium, split into two tubes each containing 10 ml seed medium, and incubated at 34° C. for 24–48 hours. One ml of culture was then used to inoculate a 125 ml DeLong Bellco Culture Flask containing 40 ml of seed medium. The inoculated culture was incubated at 33±1° C. for 24 hours in a Coy Anaerobic Chamber (Coy Laboratory Products Inc., Grass Lake, Mich.).

Fermentation

BASAL FERMENTATION MEDIUM COMPOSITION: Basal fermentation medium was prepared from the following components (per 1 L of medium):

TABLE 2

| Glucose | 7.5 g |
|---|---|
| NaCl | 5.0 g |
| $Na_2HPO_4$ | 0.5 g |
| $KH_2PO_4$ | 0.175 g |
| $MgSO_4 7H_2O$ | 0.05 g |
| Cysteine-HCl | 0.125 g |
| Tyrosine-HCl | 0.125 g |
| Powdered iron | 0.5 g |

CONTROL FERMENTATION MEDIUM COMPOSITION: Control fermentation medium was prepared from the following components (per 1 L of medium):

TABLE 3

| BHI | 250.0 ml[1] |
|---|---|
| NZ-CaseTT | 15.0 g |
| Basal medium | to 1.0 L |
| pH | 6.8 |

[1]Difco Manual (pg. 288) states that 500 g of fresh beef heart corresponds to 100 g dry weight Wyeth-Lederle Vaccines & Pediatrics uses 455 g fresh beef heart to make 1 L of BHI, which should contain 91 g of dry weight. If this is correct, and BHI contains 91 g beef liver dry weight/L, then 250 ml BHI corresponds to 22.75 g dry weight of beef heart infusion.

Basal medium was first prepared and adjusted to pH 6.8. BHI was then prepared, adjusted to pH 6.8 with 5 N NaOH, and added to basal medium. NZ-CaseTT was then prepared, added to basal medium+BHI, and dissolved by addition of HCl. pH was then adjusted to 6.8 with 5 N NaOH. Medium was distributed in 8 ml aliquots in 16×100 mm test tubes, and was autoclaved for 25 min at 121° C.

TEST FERMENTATION MEDIUM COMPOSITION: Test fermentation media were prepared by substituting a test nitrogen source for the BHI present in the control fermentation medium. Test nitrogen sources included: Hy-Soy (Quest), AMI-Soy (Quest), NZ-Soy (Quest), NZ-Soy BL4 (Quest), NZ-Soy BL7 (Quest), Sheftone D (Sheffield), SE50M (DMV), SE50 (DMV), SE%)MK (DMV), Soy Peptone (Gibco), Bacto-Soyton (Difco), Nutrisoy 2207 (ADM), Bakes Nutrisoy (ADM) Nutrisoy flour, Soybean meal, Bacto-Yeast Extract (Difco) Yeast Extract (Gibco), Hy-Yest 412 (Quest), Hy-Yest 441 (Quest), Hy-Yest 444 (Quest), Hy-Yest (455 (Quest) Bacto-Malt Extract (Difco), Corn Steep, and Proflo (Traders).

Test media were prepared as described above for control medium except that BHI was not utilized and the relevant nitrogen source was first adjusted to pH 6.8 with 3 N HCl or 5 N NaOH. Media were distributed in 8 ml aliquots per 16×100 mm test tubes, and were autoclaved for 25 min at 121° C.

CULTIVATION: A 40 μl aliquot of seed culture was used to inoculate each 8 ml control or test fermentation medium aliquot in an 8 ml 16×100 mm test tube. Cultures were then incubated at 33±1° C. for 24 hours. Tubes were incubated in an anaerobic chamber to allow for growth. Each medium test was performed in triplicate (i.e., involved three independent inoculations of the same medium), and further included a non-inoculated control (used to blank the spectrophotometer). Growth (OD) was measured every 24 hours with a Turner Spectrophotometer (Model 330) at 660 nm. Cultivation was ceased after cell lysis had lasted for about 48 hours; toxin production was measured at that point.

Preparation of Fermentation Medium

COMPOSITION OF HY-SOY FERMENTATION MEDIUM: Experiments were performed with an Hy-Soy fermentation medium containing the following components per 1 L of medium:

TABLE 4

| Hy-Soy | 35.0 g |
|---|---|
| Glucose | 7.5 g |
| NaCl | 5.0 g |
| Na$_2$HPO$_4$ | 0.5 g |
| MgSO$_4$7H$_2$O | 0.05 g |
| KH$_2$PO$_4$ | 0.175 g |
| L-Cysteine | 0.125 g |
| L-Tyrosine | 0.125 g |
| Powdered iron | 0.5 g |
| pH | 6.8 |

COMPOSITION OF M&M FERMENTATION MEDIUM: M&M medium was prepared containing the following components per liter of medium (see Mueller & Miller, *J. Bacteriol.* 67:271, 1954):

TABLE 5

| NZ-CaseTT | 22.5 g |
|---|---|
| BHI | 50.0 ml |
| Glucose | 11.0 g |
| NaCl | 2.5 g |
| Na$_2$HPO$_4$ | 2.0 g |
| MgSO$_4$7H$_2$O | 0.150 g |
| KH$_2$PO$_4$ | 0.150 g |
| L-Cysteine | 0.250 g |
| L-Tyrosine | 0.500 g |
| Powdered iron | 0.5 g |
| Ca-pantothenate | 1.0 mg |
| Uracil | 2.5 mg |
| Thiamine | 0.25 mg |
| Riboflavin | 0.25 mg |
| Pyridoxine | 0.25 mg |
| Biotin | 2.5 µg |
| pH | 7.0 |

PREPARATION OF FERMENTATION MEDIUM FOR POWDERED IRON AUTOCLAVE TEST: An incomplete fermentation medium was prepared that was lacking powdered iron, and its pH was adjusted to 6.8 with 5 N NaOH. Two sets of tubes were then prepared, one in which powdered iron was introduced into tubes, autoclaved, and then combined with 8 ml incomplete medium (per tube) that had been separately autoclaved; and one in which powdered iron was introduced into tubes, 8 ml of incomplete medium was added, and the mixture was subsequently autoclaved.

CULTIVATION: For control and test media, *C. tetani* cultivation was performed in fermentation media as described below.

Analysis of Tetanus Toxin Production

CULTURE PROCESSING: Cultured cells were centrifuged, and the pH of the supernatant was determined.

MEASUREMENT OF TETANUS TOXIN PRODUCTION PARAMETERS: The levels of Tetanus Toxin in a given sample are measured by adding a standard antitoxin and measuring the elapsed time before flocculation. Both Kf (the time required for flocculation to occur, in minutes) and Lf (the limit of flocculation; equivalent to 1 international unit of standard antitoxin, as established by flocculation) were determined. 4 ml of fermentation broth were taken from each fermentation tube for a given culture, and were combined together so that 12 ml total were mixed in a 15 ml centrifuge tube. The tubes were centrifuged at 5000 rpm (3400×g) for 30 min at 4° C. 1 ml aliquots of supernatant were then added to tubes containing 0.1–0.6 ml of standard Tetanus antiserum, and the tubes were carefully shaken to mix their contents. The tubes were then placed in a water bath at 45±1° C. and the initial time was recorded. Tubes were checked frequently, and the time at which flocculation began was recorded as Kf. The concentration of toxin in the tube in which flocculation was first initiated was designated LfFF. The concentration of toxin in the tube in which flocculation was initiated second was designated LfF.

An alternative procedure may be used to minimize that amount of antitoxin used. In this alternative procedure, 7.5 ml of fermentation broth (2.5 ml from each tube) was placed in a 15 ml centrifuge tube, mixed and centrifuged at 5000 rpm (3440×g) for 30 min at 4° C. The supernatant was used for the Lf-determination of toxin. 18.8 μl, 37.5 μl, 56.3 μl, 75.0 μl, 93.8 μl, or 112.5 μl of standard tetanus antiserum was pipetted into a series of 6×50 mm borosilicate glass round-bottom tubes. To each tube was added 187.5 μl test supernatant. The tube contents were mixed by vortexing and placed in a water bath at 45±1° C. The time was noted and the tubes were examined frequently. The time at which flocculation first occurred in a tube was recorded and noted as Kf. The tube showing the first flocculation was designated as LfFF and the second tube as LfF.

Preferably, the fermentation of *C. tetani* in media free of animal products and inoculated from cultures also free of animal products with soy-base products replacing these animal products produces an $Lf_{toxin}$ of approximately 50 or more. Minimally, $Lf_{toxin}$ equals approximately 10. Preferably the $Lf_{toxin}$ is at least 20. Most preferably the $Lf_{toxin}$ in is greater than 50.

CALCULATION OF AMOUNT OF TETANUS TOXIN: The Lftoxin value is determined from the LfFF and LfF values as follows:

LfFF>LfF Lftoxin=LfFF−(LfFF−LfF)/4

LfFF<LfF Lftoxin=LfFF+(LfF−LfFF)/4.

Example 1

Comparison of Media Containing Different Iron Sources

The purpose of this experiment was to compare the color, clarity, and pH of media containing powdered Fe, $Fe^{++}$, and $Fe^{+++}$. Four different media were prepared and analyzed as presented below:

TABLE 6

| | | No iron | Iron powder (Fe) 0.5 g/L | Ferrous sulfate (Fe++) 2.5 g/L | Ferric sulfate (Fe+++) 2.1 g/L |
|---|---|---|---|---|---|
| BEFORE | COLOR | tea | tea | green | orange |
| AUTO- | CLARITY | clear | clear | clear | cloudy |
| CLAVING | pH | 6.8 | 6.8 | 6.8 | 6.8 |
| AFTER | COLOR | tea | tea | gray | light tea |
| AUTO- | CLARITY | clear | clear | cloudy | clear |
| CLAVING | pH | 6.6 | 6.7 | 6.0 | 5.2 |

The results presented above indicate that the iron powder is the best for experiments involving optical determination of cell growth.

Example 2

Analyzing BHI and NZ-CaseTT Requirements

The purpose of this experiment was to determine the need for BHI and NZ-CaseTT for cell growth by *C. tetani* in fermentation media. The control medium in this Example is described below.

TABLE 7

| Beef heart infusion (BHI) | 250 ml/l |
|---|---|
| NZ-CaseTT | 15 g/l |
| Glucose | 7.5 g/l |
| NaCl | 5.0 g/l |
| $Na_2HPO_4$ | 0.5 g/l |
| $KH_2PO_4$ | 175 mg/l |
| $MgSO_4 \cdot 7H_2O$ | 0.05 g/l |
| L-cystine-HCl | 125 mg/l |
| L-tyrosine-HCl | 125 mg/l |
| Iron Powdered | 0.5 g/l |
| pH | 6.8 |

Media were tested as follows:

TABLE 7a

| Part | Media | Growth ($OD_{660}$) | | | | |
|---|---|---|---|---|---|---|
| | | 1(d) | 2(d) | 3(d) | 4(d) | 5(d) |
| A | Control | 0.38 | 0.61 | 0.81 | 0.70 | 0.31 |
| | Without BHI | 0.12 | 0.14 | 0.14 | 0.06 | 0.01 |
| B | Control | 0.43 | 0.62 | 0.85 | 0.56 | 0.31 |
| | Without NZ-CaseTT | 0.06 | 0.05 | 0.05 | 0.05 | 0.05 |

The results obtained, which are graphically represented in FIG. 1, indicate that (i) it is possible to follow *C. tetani* growth by $OD_{660}$; and (ii) both BHI and NZ-CaseTT are required for good growth of *C. tetani*.

Example 3

Ability of Soy Products to Replace BHI for Growth in Fermentation Media

The purpose of this experiment was to evaluate the ability of various soy products to support *C. tetani* growth in fermentation media lacking BHI. Media were tested as follows:

TABLE 8

| BHI Replacement | g/l | Growth ($OD_{660}$) | | | | |
|---|---|---|---|---|---|---|
| | | 1(d) | 2(d) | 3(d) | 4(d) | 5(d) |
| Control (BHI) | 22.75 | 0.47 | 0.67 | 0.92 | 0.55 | 0.38 |
| Hy-Soy (Sheffield) | 6.25 g | 0.39 | 0.63 | 0.76 | 0.33 | 0.21 |
| | 12.50 g | 0.43 | 0.67 | 0.79 | 0.42 | 0.29 |
| | 25.00 g | 0.49 | 0.75 | 1.00 | 0.59 | 0.51 |
| Soy peptone (Gibco) | 6.25 g | 0.45 | 0.68 | 0.78 | 0.25 | 0.22 |
| | 12.50 g | 0.51 | 0.77 | 0.90 | 0.30 | 0.24 |
| | 25.00 g | 0.62 | 0.79 | 0.90 | 0.39 | 0.32 |
| Bac-Soytone (Difco) | 6.25 g | 0.43 | 0.68 | 0.82 | 0.29 | 0.21 |
| | 12.50 g | 0.51 | 0.77 | 0.83 | 0.39 | 0.26 |
| | 25.00 g | 0.61 | 0.90 | 0.91 | 0.63 | 0.44 |
| Hy-Soy T** (Sheffield) | 6.25 g | 0.42 | 0.60 | 0.66 | 0.35 | 0.26 |
| | 12.50 g | 0.37 | 0.61 | 0.71 | 0.42 | 0.29 |
| Nutrisoy flour** | 6.25 g | 0.32 | 0.51 | 0.49 | 0.39 | 0.22 |
| | 12.50 g | 0.33 | 0.41 | 0.47 | 0.32 | 0.20 |
| Soybean meal** | 6.25 g | 0.39 | 0.57 | 0.53 | 0.33 | 0.12 |
| | 12.50 g | 0.41 | 0.62 | 0.45 | 0.26 | 0.13 |
| Bake Nutrisoy** (ADM) | 6.25 g | 0.38 | 0.58 | 0.50 | 0.38 | 0.18 |

**Water-insoluble soy products

Figure 2:
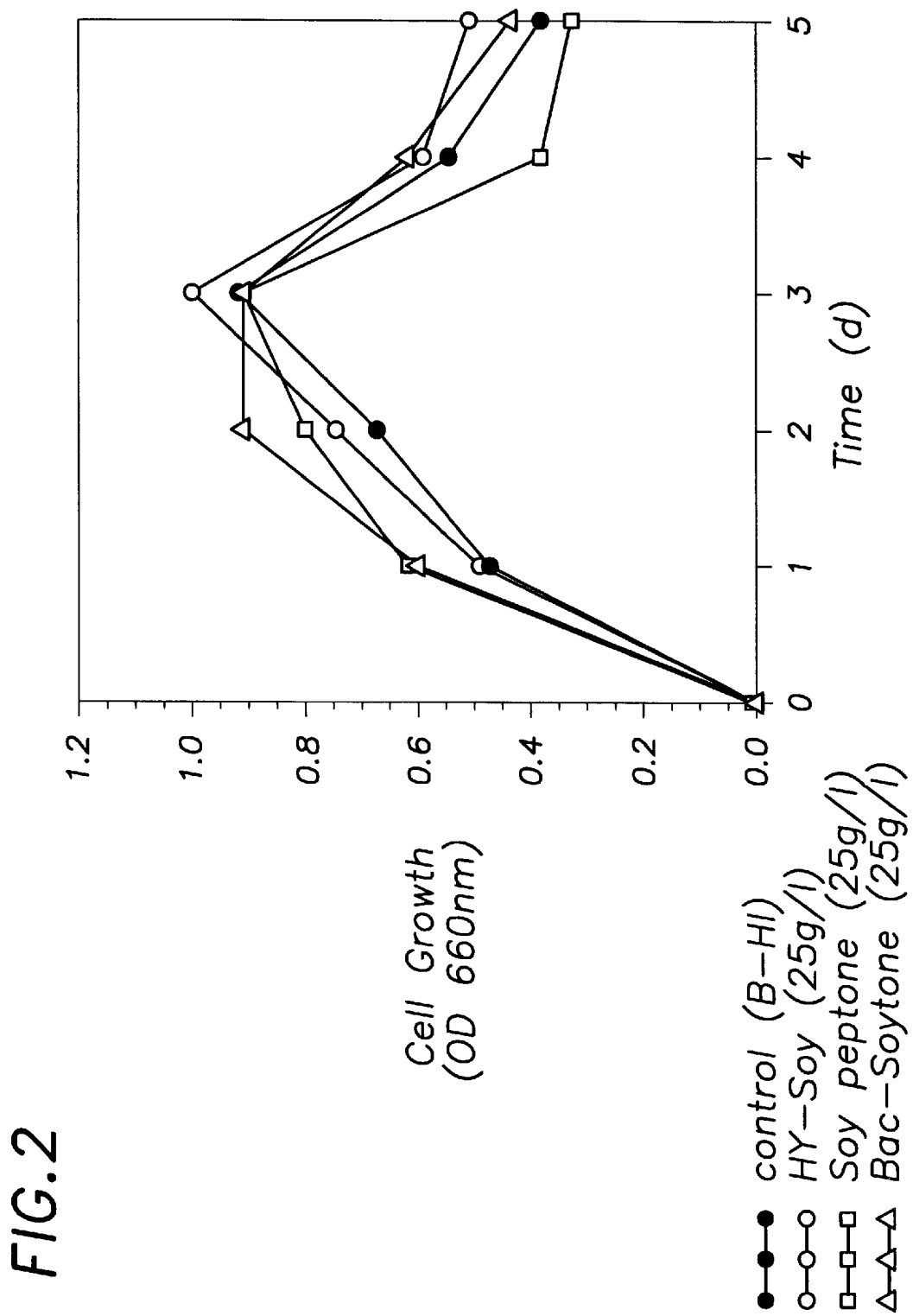
FIG. 2 depicts the ability of various soluble soy products to replace BHI in fermentation media supporting growth of *C. tetani*.
Figure 3:
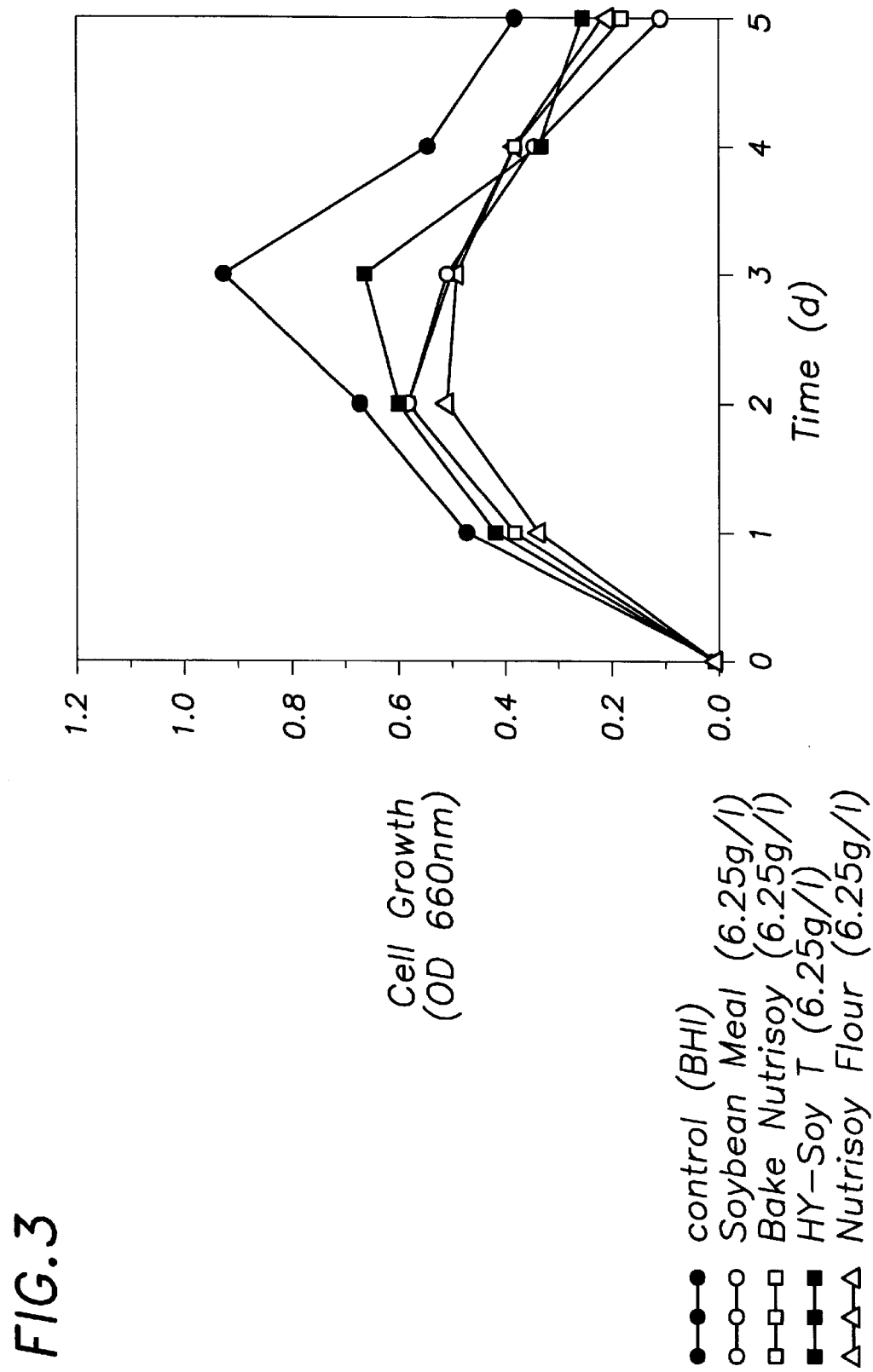
FIG. 3 depicts the ability of various insoluble soy products to replace BHI in fermentation media supporting growth of *C. tetani*.

The results obtained, which are graphically represented in FIGS. 2 and 3, indicated that soluble soy preparations could replace BHI for growth of *C. tetani*. The best concentration appeared to be 12.5 or 25 g/L. Hy-Soy (Sheffield) gave the highest growth. Insoluble soy preparations were less effective.

Example 4

Ability of Additional Soy Products to Replace BHI for Growth in Fermentation Media The purpose of this experiment was to test the ability of additional soy products to replace BHI in fermentation media supporting growth of *C. tetani*. Media were tested as follows:

TABLE 9

| BHI Replacement | g/l | Growth ($OD_{660}$) | | | | |
|---|---|---|---|---|---|---|
| | | 1(d) | 2(d) | 3(d) | 4(d) | 5(d) |
| Control (BHI) | 22.75 (250 ml) | 0.38 | 0.61 | 0.81 | 0.70 | 0.31 |
| Hy-Soy (Quest) | 6.25 g | 0.32 | 0.57 | 0.71 | 0.63 | 0.23 |
| | 25.00 g | 0.40 | 0.68 | 0.91 | 0.84 | 0.47 |
| AMISOY (Quest) | 6.25 g | 0.40 | 0.56 | 0.59 | 0.44 | 0.24 |
| | 25.00 g | 0.47 | 0.56 | 0.53 | 0.20 | 0.04 |
| NZ Soy (Quest) | 6.25 g | 0.31 | 0.57 | 0.75 | 0.52 | 0.30 |
| | 25.00 g | 0.48 | 0.74 | 0.91 | 0.40 | 0.27 |
| NZ Soy BL4 (Quest) | 6.25 g | 0.28 | 0.60 | 0.71 | 0.61 | 0.47 |
| | 25.00 g | 0.16 | 0.47 | 0.73 | 0.66 | 0.51 |
| NZ Soy BL7 (Quest) | 6.25 g | 0.32 | 0.58 | 0.69 | 0.54 | 0.33 |
| | 25.00 g | 0.38 | 0.59 | 0.69 | 0.56 | 0.29 |
| SE50M (DMV) | 6.25 g | 0.34 | 0.58 | 0.69 | 0.59 | 0.29 |
| | 25.00 g | 0.36 | 0.38 | 0.69 | 0.65 | 0.27 |
| SE50MK (DMV) | 6.25 g | 0.31 | 0.60 | 0.77 | 0.81 | 0.57 |
| | 25.00 g | 0.43 | 0.69 | 0.91 | 0.97 | 0.57 |
| Soy peptone (Gibco) | 6.25 g | 0.31 | 0.63 | 0.77 | 0.75 | 0.34 |
| | 25.00 g | 0.47 | 0.59 | 0.83 | 0.45 | 0.30 |
| Bac-Soytone (Difco) | 6.25 | 0.30 | 0.63 | 0.79 | 0.47 | 0.21 |
| | 25.00 | 0.43 | 0.79 | 0.88 | 0.42 | 0.40 |

Figure 4:
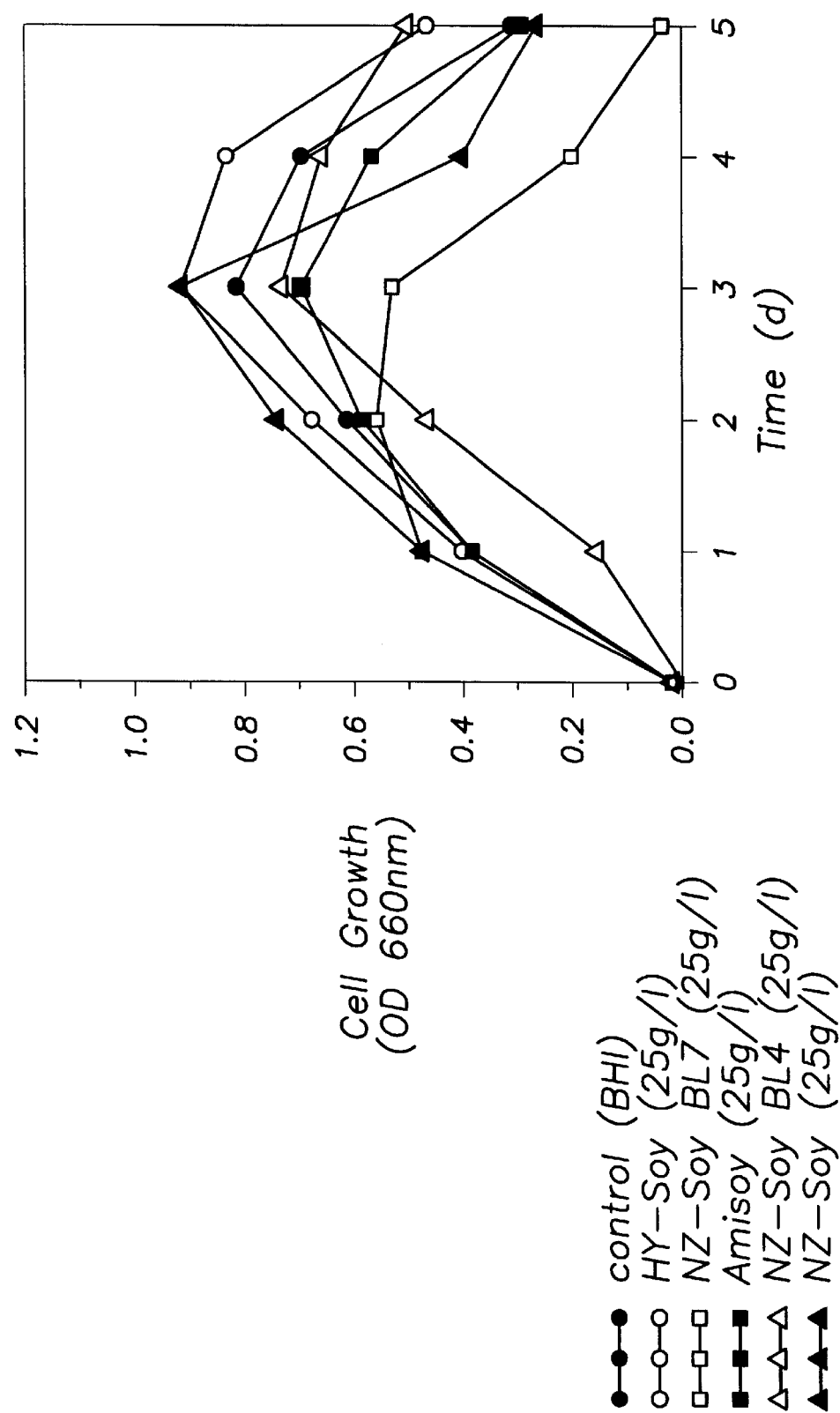
FIG. 4 depicts the ability of various soluble soy products to replace BHI in fermentation media supporting growth of *C. tetani*.
Figure 5:
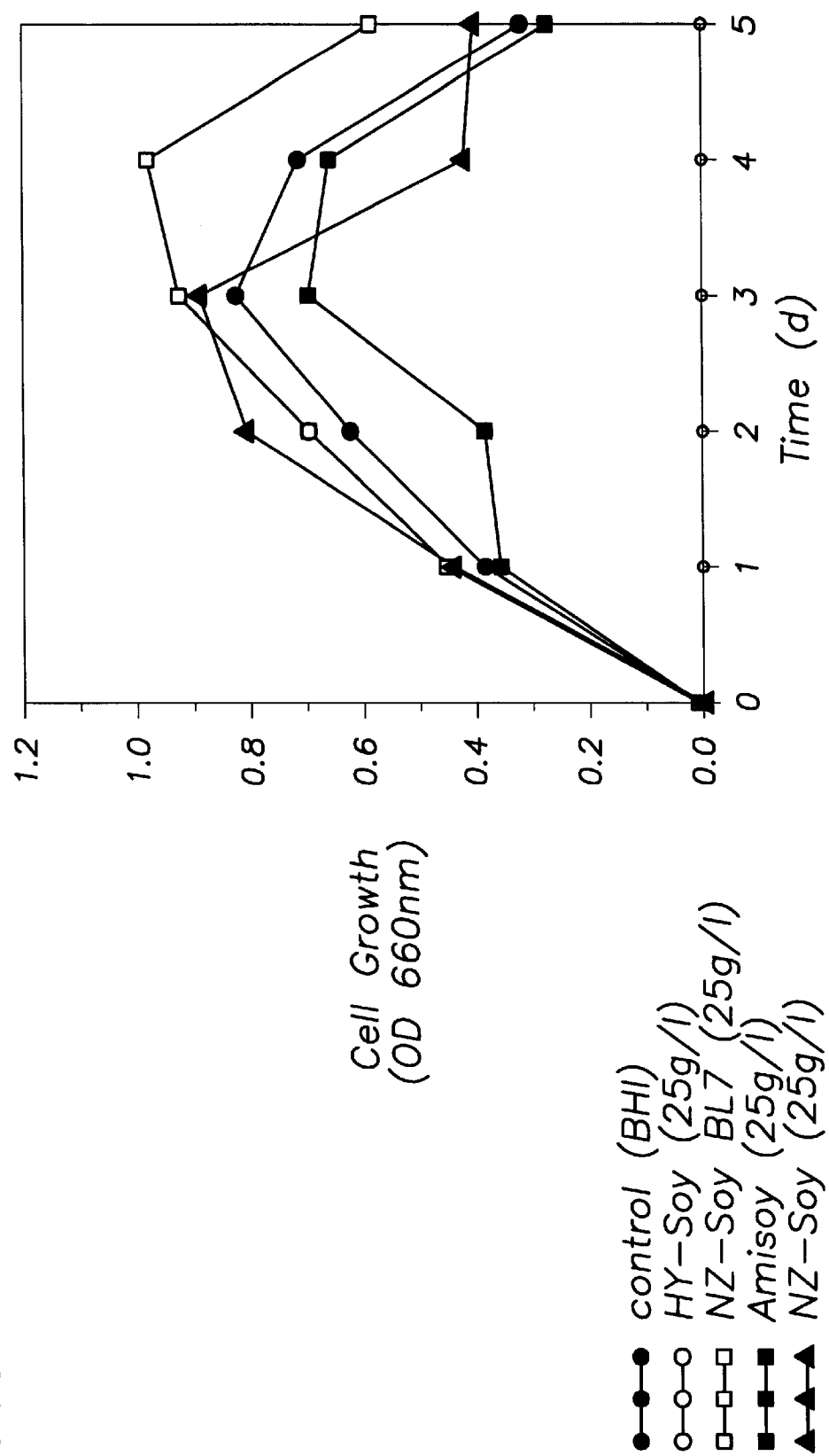
FIG. 5 depicts the ability of various soluble soy products to replace BHI in fermentation media supporting growth of *C. tetani*.

The results obtained, which are graphically represented in FIGS. 4 and 5, indicate that a variety of different soy products are capable of supporting *C. tetani* growth in fermentation media in the absence of BHI. SE50MK at 25 g/L gave the best results. Quest Hy-Soy is most likely the same product as Sheffield Hy-Soy used in Example 3.

Example 5

Ability of Soy Products to Support Toxin Production in Fermentation Media

The purpose of this experiment was two-fold: (i) to confirm the observation, reported above in Examples 3 and 4, that soy products are able to replace BHI for *C. tetani* growth; and (ii) to test the ability of these soy products to support Tetanus Toxin production by *C. tetani*. Media were tested for their ability to support *C. tetani* growth as follows:

TABLE 10

| BHI Replacement | g/l | Growth ($OD_{660}$)* | | | | |
|---|---|---|---|---|---|---|
| | | 1(d) | 2(d) | 3(d) | 4(d) | 5(d) |
| BHI (250 ml) | 22.75 | 0.45 | 0.63 | 0.71 | 0.53 | 0.39 |
| (375 ml) | 34.13 | 0.52 | 0.77 | 0.97 | 0.50 | 0.38 |
| Hy-Soy (Quest) | 22.75 | 0.45 | 0.77 | 0.94 | 0.54 | 0.37 |
| | 34.13 | 0.50 | 0.83 | 1.02 | 0.69 | 0.63 |
| NZ Soy (Quest) | 22.75 | 0.49 | 0.75 | 0.65 | 0.39 | 0.30 |
| | 34.13 | 0.61 | 0.87 | 0.65 | 0.46 | 0.39 |
| NZ Soy BL4 (Quest) | 22.75 | 0.50 | 0.79 | 0.83 | 0.79 | 0.63 |
| | 34.13 | 0.58 | 0.83 | 0.92 | 0.90 | 0.75 |
| NZ Soy BL7 (Quest) | 22.75 | 0.46 | 0.64 | 0.63 | 0.42 | 0.28 |
| | 34.13 | 0.46 | 0.67 | 0.65 | 0.49 | 0.31 |
| SE50M (DMV) | 22.75 | 0.47 | 0.59 | 0.80 | 0.35 | 0.26 |
| | 34.13 | 0.55 | 0.60 | 0.83 | 0.49 | 0.42 |

TABLE 10-continued

| BHI Replacement | g/l | 1(d) | 2(d) | 3(d) | 4(d) | 5(d) |
|---|---|---|---|---|---|---|
| SE50MK | 22.75 | 0.42 | 0.77 | 0.93 | 0.89 | 0.46 |
| (DMV) | 34.13 | 0.53 | 0.82 | 1.10 | 0.88 | 0.69 |
| Soy peptone | 22.75 | 0.51 | 0.73 | 0.89 | 0.49 | 0.29 |
| (Gibco) | 34.13 | 0.56 | 0.73 | 0.92 | 0.48 | 0.41 |
| Bac-Soytone | 22.75 | 0.49 | 0.84 | 0.93 | 0.48 | 0.34 |
| (Difco) | 34.13 | 0.55 | 0.97 | 0.90 | 0.59 | 0.51 |

*Before fermentation, the $OD_{660}$ was <0.01.

Figure 6:
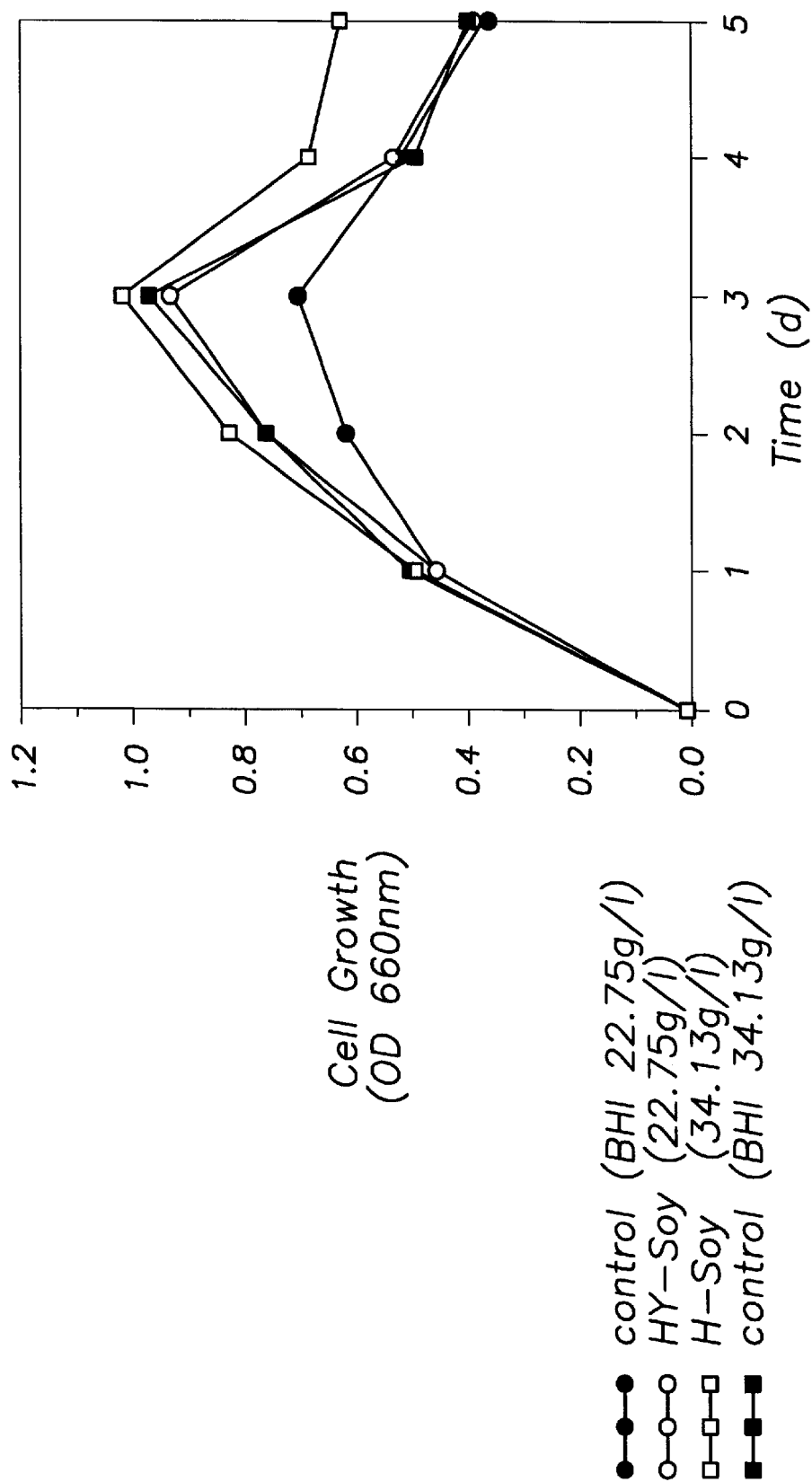
FIG. 6 shows a comparison of *C. tetani* cell growth supported by two different concentrations of BHI and two different concentrations of HY-Soy (Quest).
Figure 7:
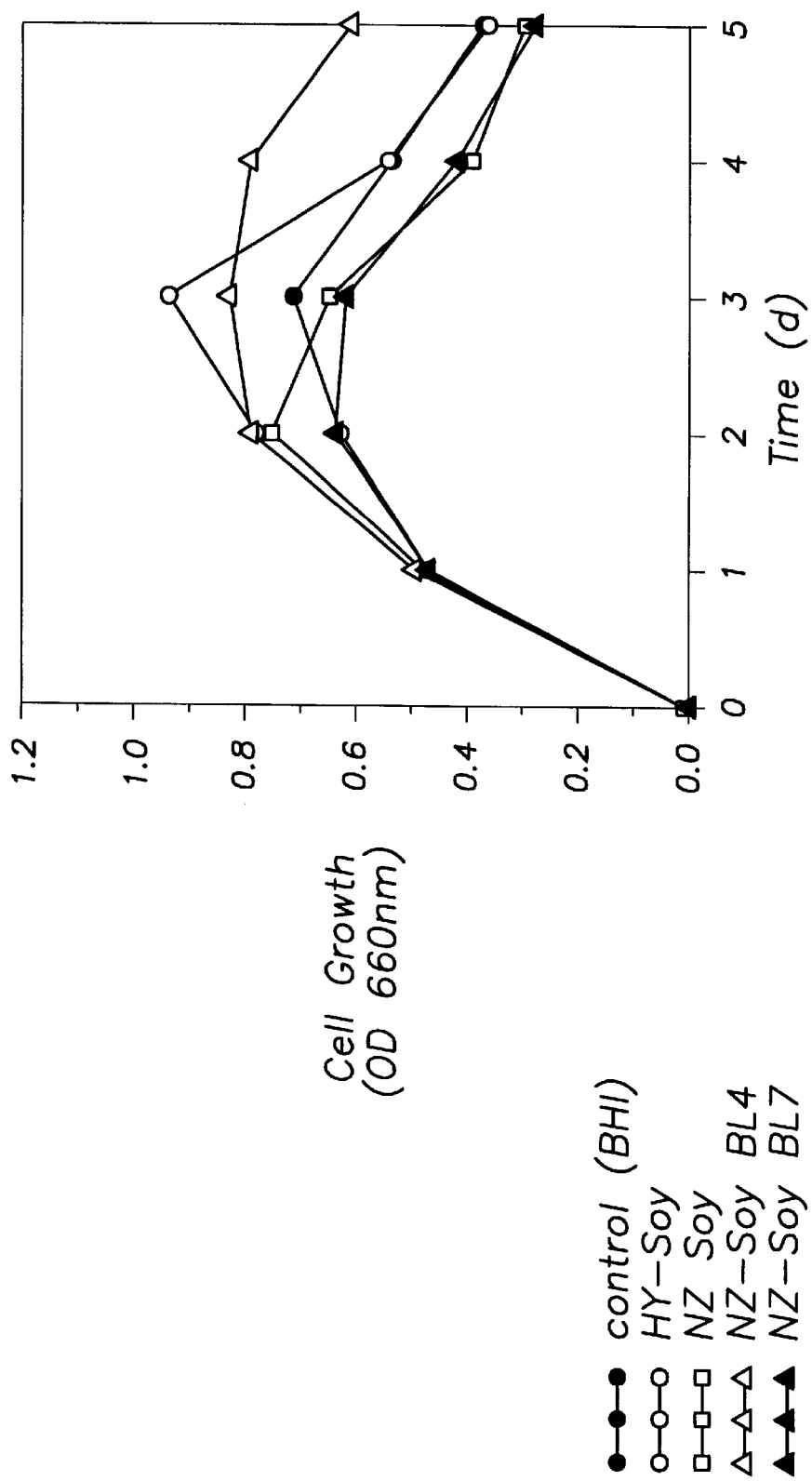
FIG. 7 shows the ability of various soy products, present at 22.75 g/L, to replace BHI in fermentation media supporting growth of *C. tetani*.
Figure 8:
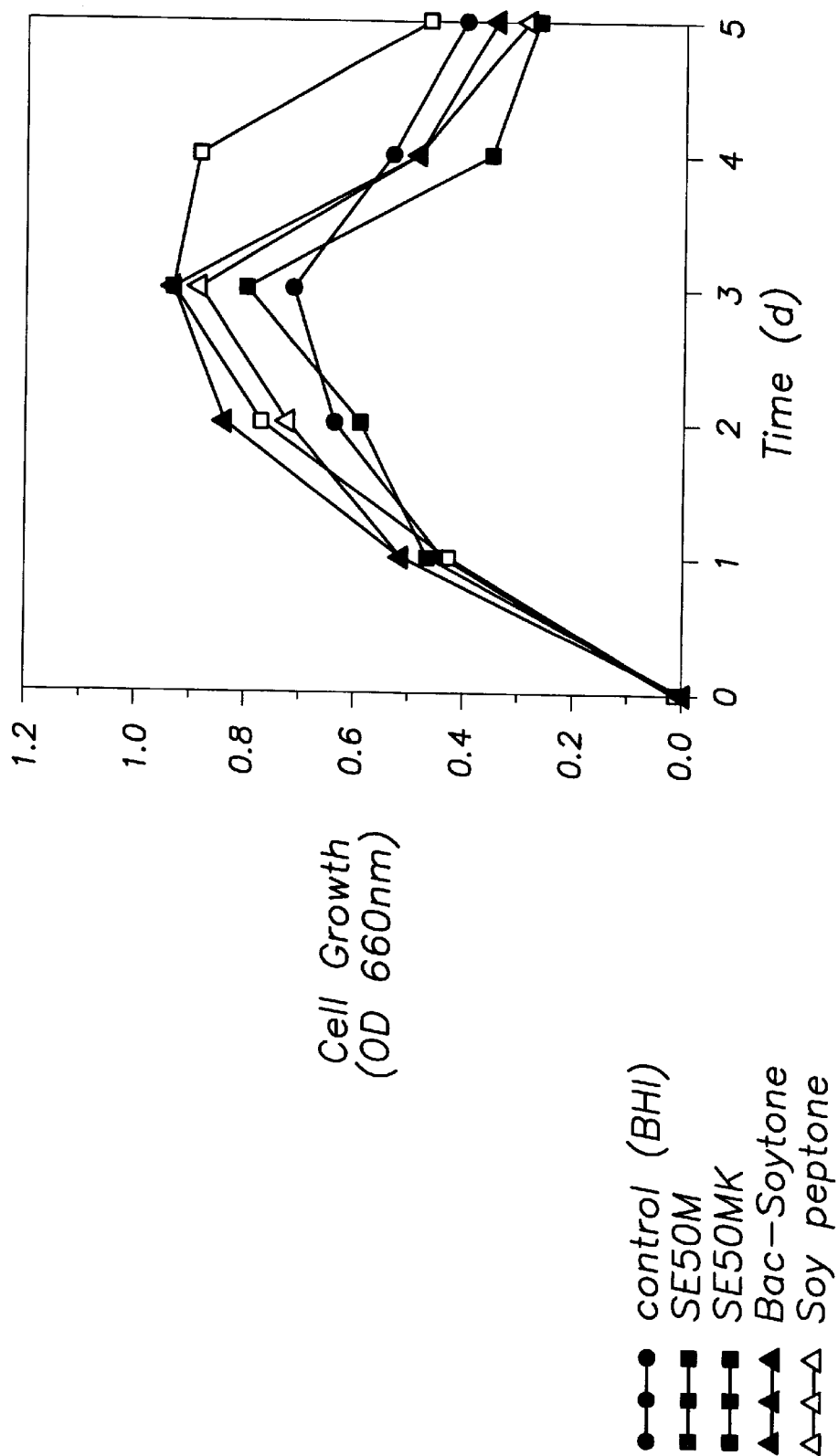
FIG. 8 shows the ability of various soy products, present at 22.75 g/L, to replace BHI for cell growth.
Figure 11:
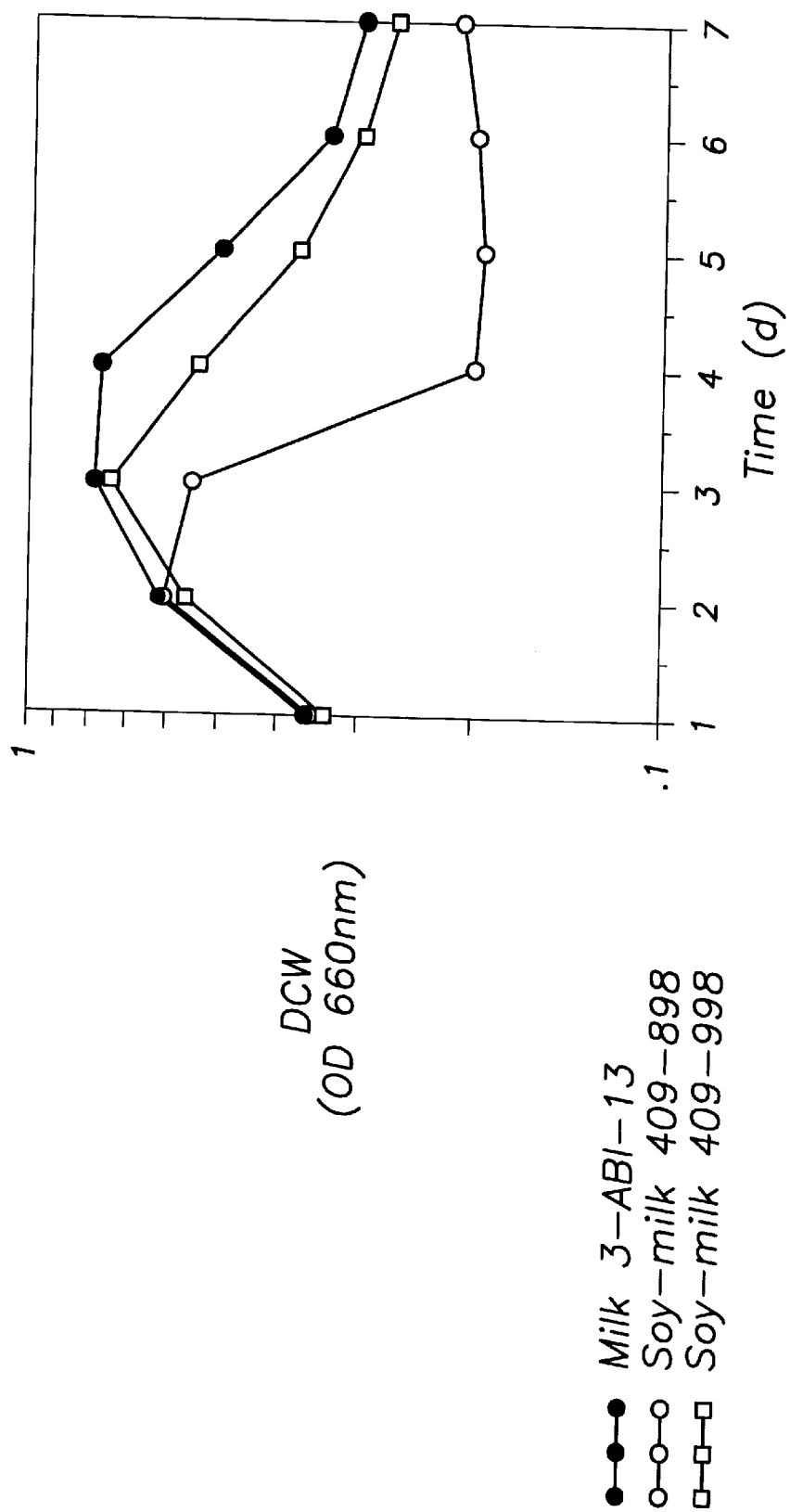
FIG. 11 is a graph showing the growth of *C. tetani* in the soy-based fermentation medium with inoculants originating from cultures of *C. tetani* lyophilized in animal milk or soy milk.
Figure 12:
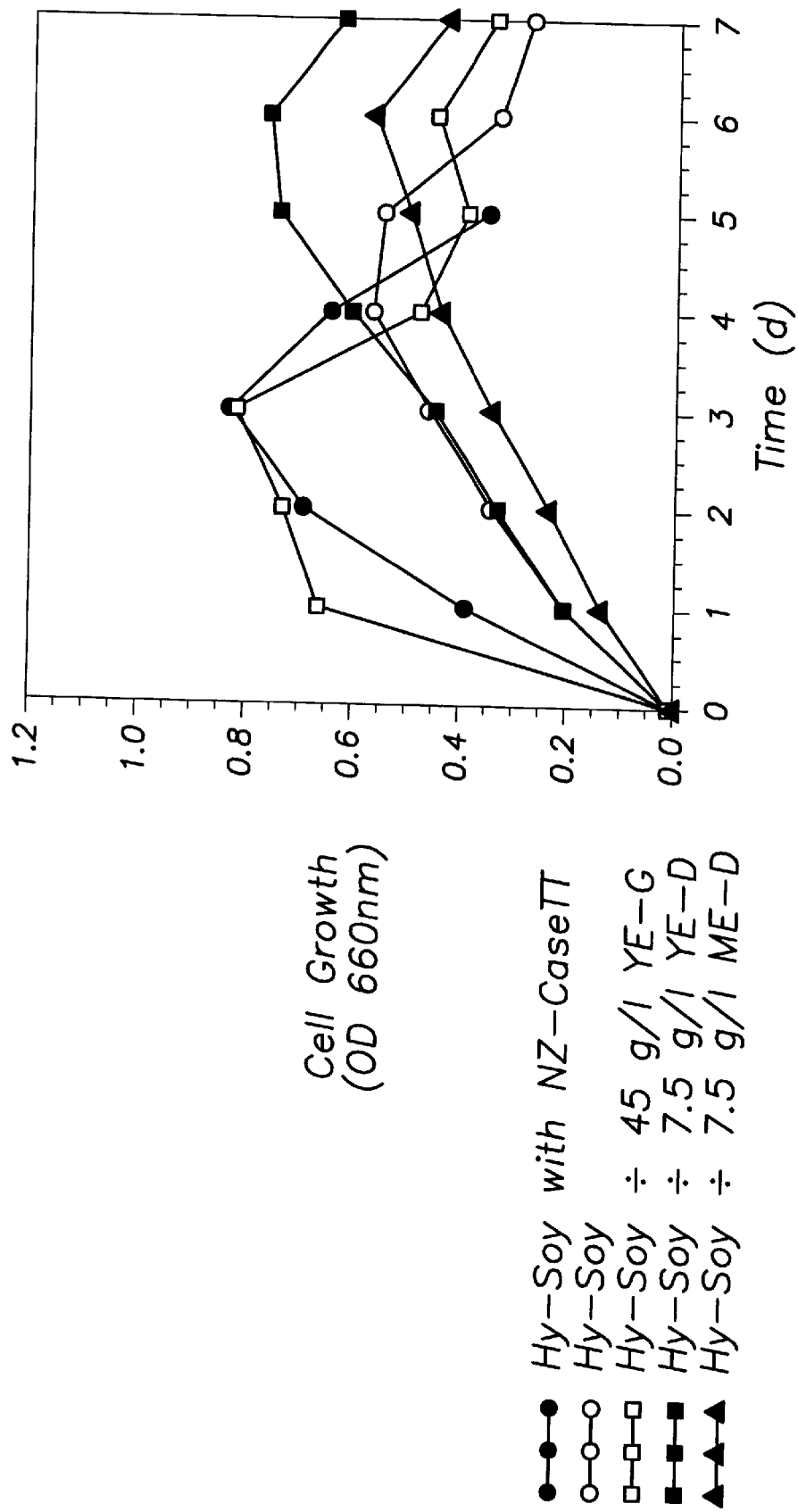
FIG. 12 is a graph depicting growth of *C. tetani* in fermentation media containing yeast extracts or malt extracts as replacements for NZ-CaseTT.

The results obtained, which are graphically represented in FIGS. 6, 7, and 8, indicate that Quest Hy-Soy, DMV SE50MK, and Quest NZ-Soy were effective soy products in terms of their ability to replace BHI for *C. tetani* growth. These products were also able to replace BHI at a higher level than levels analyzed in prior Examples.

Media were also tested for their ability to support toxin production, as follows:

TABLE 11

| BHI Replacement | (g/l) | LfFF | LfF | Lftoxin |
|---|---|---|---|---|
| BHI (250 ml) | 22.75 | 30 | 20 | 27.5 |
| (375 ml) | 34.13 | 30 | 40 | 32.5 |
| Hy-Soy | 22.75 | 50 | 60 | 52.5 |
| (Quest) | 34.13 | 40 | 30 | 37.5 |
| NZ Soy | 22.75 | 20 | 10 | 17.5 |
| (Quest) | 34.13 | 30 | 20 | 27.5 |
| NZ Soy BL4 | 22.75 | — | — | — |
| (Quest) | 34.13 | — | — | — |
| NZ Soy BL7 | 22.75 | — | — | — |
| (Quest) | 34.13 | — | — | — |
| SB50M | 22.75 | — | — | — |
| (DMV) | 34.13 | — | — | — |
| SE50MK | 22.75 | 40 | 30 | 37.5 |
| (DMV) | 34.13 | — | — | — |
| Soy peptone | 22.75 | — | — | — |
| (Gibco) | 34.13 | — | — | — |
| Bac-Soytone | 22.75 | — | — | — |
| (Difco) | 34.13 | — | — | — |

Reaction done in a water bath at 46 ± 1° C. (--) In this table and all subsequent tables, --indicates the lack of flocculation in the toxin assay.

The results presented above, which represent analyses of toxin present in 5th day broth, reveal that the soy products (such as Quest Hy-Soy, DMV SE50MK, and Quest NZ-Soy) that were optimal for growth were also effective at replacing BHI for toxin production. The best soy product for toxin production was Quest Hy-Soy at 22.75 g/l. Interestingly, higher concentrations of this product produced better growth but did not improve toxin production. Similar results were obtained with SE50MK, for which a higher concentration generated increased growth but did not increase toxin production. NZ-Soy, on the other hand, gave higher growth and higher toxin production at its higher concentration.

We tested the pH of our various fermentation media as made up, before and after autoclaving, and before and after fermentation. We found, as shown below, that pH rose during fermentation, but its final value did not correlate with growth or production.

TABLE 12

| BHI Replacement | (g/l) | pH of Medium before adjustment | pH of Medium before autoclaving | Broth after autoclaving, before fermentation | Broth after fermentation |
|---|---|---|---|---|---|
| BHI (250 ml) | 22.75 | 6.2 | 6.8 | 6.5 | 7.1 |
| (375 ml) | 34.13 | 6.2 | 6.8 | 6.5 | 7.4 |
| Hy-Soy | 22.75 | 7.1 | 6.8 | 6.6 | 7.5 |
| (Quest) | 34.13 | 7.1 | 6.8 | 6.6 | 7.6 |
| NZ Soy | 22.75 | 6.6 | 6.8 | 6.5 | 7.5 |
| (Quest) | 34.13 | 6.6 | 6.8 | 6.4 | 7.6 |
| NZ Soy BL4 | 22.75 | 4.0 | 6.8 | 6.4 | 6.4 |
| (Quest) | 34.13 | 4.0 | 6.8 | 6.4 | 6.5 |
| NZ Soy BL7 | 22.75 | 7.1 | 6.8 | 6.4 | 6.6 |
| (Quest) | 34.13 | 7.1 | 6.8 | 6.4 | 6.6 |
| SE50M | 22.75 | 7.4 | 6.8 | 6.5 | 7.3 |
| (DMV) | 34.13 | 7.4 | 6.8 | 6.6 | 7.5 |
| SE50MK | 22.75 | 7.3 | 6.8 | 6.6 | 7.2 |
| (DMV) | 34.13 | 7.3 | 6.8 | 6.5 | 7.4 |
| Soy peptone | 22.75 | 7.0 | 6.8 | 6.5 | 7.2 |
| (Gibco) | 34.13 | 7.0 | 6.8 | 6.5 | 7.4 |
| Bac-Soytone | 22.75 | 7.1 | 6.8 | 6.5 | 7.0 |
| (Difco) | 34.13 | 7.1 | 6.8 | 6.5 | 7.3 |

Example 6

Ability of Soy Products to Replace NZ-CaseTT for Growth and Toxin Production in Fermentation Media The purpose of this experiment was to determine whether NZ-CaseTT was required for cell growth and toxin production when BHI had been replaced with a soy product. The effect of NZ-CaseTT removal on cell growth is presented for a variety of different media (where BHI or soy product was used at a concentration of 22.75 g/L) below in Table 13, and also in FIG. 9:

TABLE 13

| BHI Replacement (at 22.75 g/l) | 1(d) | 2(d) | 3(d) | 4(d) | 5(d) |
|---|---|---|---|---|---|
| With NZ-CaseTT (15 g/l) | | | | | |
| Control (BHI) | 0.43 | 0.62 | 0.85 | 0.56 | 0.31 |
| HY-Soy | 0.40 | 0.71 | 0.94 | 0.79 | 0.45 |
| NZ-Soy | 0.49 | 0.77 | 0.83 | 0.32 | 0.23 |
| SE50MK | 0.48 | 0.76 | 1.00 | 0.71 | 0.50 |
| Without NZ-CaseTT | | | | | |
| Control (BHI) | 0.06 | 0.05 | 0.05 | 0.05 | 0.05 |
| HY-Soy | 0.16 | 0.27 | 0.35 | 0.45 | 0.50 |
| NZ-Soy | 0.15 | 0.23 | 0.23 | 0.24 | 0.23 |
| SE50MK | 0.28 | 0.43 | 0.55 | 0.67 | 0.45 |

*Before fermentation the $OD_{660}$ was <0.01.

These data confirm that soy products can effectively replace BHI in the presence of NZ-CaseTT, and also demonstrate that these products have some ability to replace NZ-CaseTT as well. That is, NZ-CaseTT is required for growth in BHI-based media, but is not required for growth in soy-based media. Removal of NZ-CaseTT from soy-based media reduced growth (approximately 2–4 fold), but did not eliminate it. In this experiment, the best soy product for growth both in the presence and the absence of NZ-CaseTT was SE50MK.

Example 7

Ability of Non-soy, Non-animal Products to Replace NZ-CaseTT for Growth and Toxin Production in Fermentation Media The purpose of this experiment was to test the ability of a variety of non-soy, non-animal products (Difco yeast extract, corn steep, or Proflo) to replace NZ-CaseTT for cell growth and/or for toxin production. BHI and soluble soy products were utilized at approximately 23 g/L; NZ-CaseTT and its replacements were utilized at 15 g/L. The results of the cell growth tests are presented below in Table 14, and also in FIG. 10.

TABLE 14

| BHI Replacement | Growth ($OD_{660}$)* | | | | |
|---|---|---|---|---|---|
| | 1(d) | 2(d) | 3(d) | 4(d) | 5(d) |
| With NZ-CaseTT | | | | | |
| BHI (control) | 0.43 | 0.62 | 0.85 | 0.56 | 0.31 |
| Hy-Soy | 0.40 | 0.71 | 0.94 | 0.79 | 0.45 |
| NZ-Soy | 0.49 | 0.77 | 0.83 | 0.32 | 0.23 |
| SE50MK | 0.48 | 0.76 | 1.00 | 0.71 | 0.50 |
| With yeast extract replacing NZ-CaseTT | | | | | |
| BHI | 0.28 | 0.39 | 0.47 | 0.58 | 0.57 |
| Hy-Soy | 0.32 | 0.44 | 0.50 | 0.61 | 0.67 |
| NZ-Soy | 0.64 | 0.65 | 0.69 | 0.67 | 0.49 |
| SB50MK | 0.40 | 0.49 | 0.42 | 0.45 | 0.54 |
| With corn steep replacing NZ-CaseTT | | | | | |
| BHI | 0.09 | 0.09 | 0.10 | 0.11 | 0.12 |
| Hy-Soy | 0.18 | 0.22 | 0.28 | 0.36 | 0.36 |
| NZ-Soy | 0.36 | 0.36 | 0.14 | 0.10 | 0.10 |
| SE50MK | 0.26 | 0.27 | 0.24 | 0.22 | 0.19 |
| With Proflo replacing NZ-CaseTT | | | | | |
| BHI | 0.02 | 0.01 | 0.02 | 0.02 | 0.02 |
| Hy-Soy | 0.05 | 0.10 | 0.05 | 0.03 | 0.03 |
| NZ-Soy | 0.12 | 0.09 | <0.01 | <0.01 | <0.01 |
| SE50MK | 0.08 | 0.20 | 0.01 | <0.02 | <0.01 |

*Before fermentation the $OD_{660}$ was <0.01.

As can be seen, yeast extract was able to partially replace NZ-CaseTT for growth; corn steep and Proflo were poor replacements.

Example 8

Ability of Yeast Extracts and Malt Extracts to Replace NZ-CaseTT for Growth and Toxin Production in Fermentation Media The purposes of experiments summarized in Example 8 were to compare the effects of substituting various yeast extracts and malt extracts for BHI and NZ-CaseTT in media containing Hy-Soy for growth of *C. tetani* and production of Tetanus Toxin. Table 15 summarizes data on experiments substituting yeast extracts from two sources and a malt extract for BHI and NZ-CaseTT in media containing Hy-Soy for growth of *C. tetani*.

TABLE 15

| BHI Replacement | g/l | Growth ($OD_{660}$) | | | | | | |
|---|---|---|---|---|---|---|---|---|
| | | 1(d) | 2(d) | 3(d) | 4(d) | 5(d) | 6(d) | 7(d) |
| With NZ-CaseTT | | | | | | | | |
| BHI | 22.75 | 0.46 | 0.65 | 0.80 | 0.73 | 0.33 | | |
| Hy-Soy | 22.75 | 0.39 | 0.69 | 0.83 | 0.65 | 0.35 | | |
| Without BHI & NZ-CaseTT | | | | | | | | |
| Hy-Soy | 22.75 | 0.20 | 0.34 | 0.46 | 0.56 | 0.55 | 0.33 | 0.27 |
| With Hy-Soy (22.75 g/l) & without BHI & NZ-CaseTT | | | | | | | | |
| Yeast extract (Difco) | 7.5 | 0.20 | 0.33 | 0.45 | 0.61 | 0.74 | 0.77 | 0.63 |
| | 15.0 | 0.29 | 0.42 | 0.49 | 0.61 | 0.71 | 0.75 | 0.59 |
| | 30.0 | 0.41 | 0.47 | 0.43 | 0.57 | 0.71 | 0.59 | 0.43 |
| | 45.0 | 0.57 | 0.48 | 0.58 | 0.69 | 0.49 | 0.47 | 0.42 |

TABLE 15-continued

| BHI Replacement | g/l | Growth ($OD_{660}$) | | | | | | |
|---|---|---|---|---|---|---|---|---|
| | | 1(d) | 2(d) | 3(d) | 4(d) | 5(d) | 6(d) | 7(d) |
| Yeast extract (Gibco) | 7.5 | 0.20 | 0.33 | 0.47 | 0.62 | 0.53 | 0.47 | 0.32 |
| | 15.0 | 0.25 | 0.40 | 0.50 | 0.64 | 0.55 | 0.43 | 0.35 |
| | 30.0 | 0.47 | 0.59 | 0.67 | 0.69 | 0.61 | 0.55 | 0.37 |
| | 45.0 | 0.66 | 0.73 | 0.81 | 0.48 | 0.39 | 0.45 | 0.34 |
| Malt extract (Difco) | 7.5 | 0.14 | 0.24 | 0.34 | 0.44 | 0.50 | 0.57 | 0.43 |
| | 15.0 | 0.13 | 0.20 | 0.28 | 0.37 | 0.42 | 0.50 | 0.47 |
| | 30.0 | 0.08 | 0.14 | 0.19 | 0.27 | 0.29 | 0.37 | 0.40 |
| | 45.0 | 0.07 | 0.10 | 0.12 | 0.15 | 0.19 | 0.23 | 0.28 |

Before fermentation, the $OD_{660}$ was <0.01.

The above data show that again Difco yeast extract at 15 g/l partially replaced NZ-CaseTT for growth. Lower and higher concentrations were no better. Gibco yeast extract at 45 g/l was slightly better than Difco yeast extract; lower concentrations were slightly poorer. Difco malt extract had no ability to replace NZ-CaseTT and in fact was slightly inhibitory for growth.

Table 16 shows the effects of substituting yeast extracts and malt extract for BHI and NZ-CaseTT on Tetanus Toxin production by *C. tetani* in media for growth of *C. tetani*.

TABLE 16

| BHI Replacment | (g/l) | Time (day) | Kf | $Lf_F$ | $Lf_{FF}$ | $Lf_{toxin}$ |
|---|---|---|---|---|---|---|
| With NZ-CaseTT | | | | | | |
| BHI | 250 ml | 5 | 70 | 30 | 20 | 27.5 |
| HY-Soy | 22.75 | 5 | 80 | 40 | 30 | 37.5 |
| Without BHI & NZ-CaseTT | | | | | | |
| HY-Soy | 22.75 | 7 | 60 | 40 | 30 | 37.5 |
| With HY-Soy and Without BHI & NZ-CaseTT | | | | | | |
| Yeast extract (Difco) | 7.5 | 8 | 120 | 10 | 20 | 12.5 |
| | 15.0 | 8 | — | — | — | — |
| | 30.0 | 7 | — | — | — | — |
| | 45.0 | 7 | — | — | — | — |
| Yeast extract (Gibco) | 7.5 | 7 | — | — | — | — |
| | 15.0 | 7 | — | — | — | — |
| | 30.0 | 7 | — | — | — | — |
| | 45.0 | 7 | — | — | — | — |
| Malt extract (Difco) | 7.5 | 7 | — | — | — | — |
| | 15.0 | 7 | — | — | — | — |
| | 30.0 | 7 | — | — | — | — |
| | 45.0 | 7 | — | — | — | — |

These data show that yeast extracts interfered with toxin formation even when the assay was performed on broth from the lytic phase of the growth cycle. Also, the data suggest that HY-Soy can replace both BHI and NZ-CaseTT for toxin production. However, a longer fermentation cycle of 1 or 2 days may be necessary.

Table 17 summarizes data on experiments similar to experiments depicted in Table 16 designed to study the effects of additional yeast extracts on the growth of *C. tetani* when substituted for BHI and NZ-CaseTT in growth media for *C. tetani*.

TABLE 17

| Media | g/l | 1(d) | 2(d) | 3(d) | 4(d) | 5(d) | 6(d) | 7(d) | 8(d) | 9(d) |
|---|---|---|---|---|---|---|---|---|---|---|
| *With NZ-CaseTT* | | | | | | | | | | |
| BHI | 22.75 | 0.42 | 0.64 | 0.84 | 0.72 | 0.35 | 0.26 | 0.28 | 0.30 | 0.29 |
| HY-Soy | 22.75 | 0.39 | 0.65 | 0.94 | 0.85 | 0.69 | 0.47 | 0.38 | 0.29 | 0.31 |
| *Without BHI & NZ-CaseTT* | | | | | | | | | | |
| HY-Soy | 22.75 | 0.17 | 0.34 | 0.49 | 0.56 | 0.58 | 0.38 | 0.31 | 0.27 | 0.26 |
| *With HY-Soy and Without BHI & NZ-CaseTT* | | | | | | | | | | |
| Hy-Yest 412 (Quest) | 7.5 | 0.20 | 0.23 | 0.25 | 0.28 | 0.39 | 0.53 | 0.57 | 0.44 | 0.28 |
| | 15.0 | 0.41 | 0.52 | 0.48 | 0.38 | 0.39 | 0.39 | 0.35 | | |
| | 30.0 | 0.54 | 0.58 | 0.33 | 0.27 | 0.23 | | | | |
| Hy-Yest 441 (Quest) | 7.5 | 0.19 | 0.31 | 0.39 | 0.51 | 0.64 | 0.56 | 0.50 | 0.43 | 0.37 |
| | 15.0 | 0.27 | 0.38 | 0.44 | 0.52 | 0.56 | 0.56 | 0.45 | | |
| | 30.0 | 0.55 | 0.55 | 0.49 | 0.50 | 0.44 | | | | |
| Hy-Yest 444 (Quest) | 7.5 | 0.18 | 0.30 | 0.35 | 0.55 | 0.75 | 0.75 | 0.50 | 0.40 | 0.39 |
| | 15.0 | 0.28 | 0.37 | 0.40 | 0.58 | 0.66 | 0.59 | 0.46 | | |
| | 30.0 | 0.56 | 0.60 | 0.60 | 0.50 | 0.38 | | | | |
| Hy-Yest 455 (Quest) | 7.5 | 0.24 | 0.36 | 0.47 | 0.66 | 0.81 | 0.60 | 0.45 | 0.41 | 0.41 |
| | 0.30 | 0.47 | 0.59 | 0.79 | 0.77 | 0.63 | 0.57 | | | |
| | 0.46 | 0.59 | 0.71 | 0.71 | 0.57 | | | | | |

Before fermentation, the OD660 was <0.01.

The results are similar to results summarized in Table 16. The yeast extracts with the exception of HY-Yest 412 did partially replace NZ-CaseTT for growth. The optimal concentration for growth *C. tetani* was the lowest concentration studied (7.5 g/l) for HY-Yest 441, HY-Yest 444 and HY-Yest 455.

Table 18 shows the effects of substituting yeast extracts for BHI and NZ-CaseTT on Tetanus Toxin production by *C. tetani* in growth media.

TABLE 18

| BHI Replacment | (g/l) | Time (day) | Kf | Lf $Lf_{FF}$ | $Lf_F$ | $Lf_{toxin}$ |
|---|---|---|---|---|---|---|
| | | With NZ-CaseTT | | | | |
| BHI | 22.75 | 5 | 75 | 30 | 20 | 22.5 |
| | | 7 | 60 | 30 | 40 | 32.5 |
| | | 9 | 54 | 30 | 40 | 32.5 |
| HY-Soy | 22.75 | 5 | 90 | 30 | 20 | 27.5 |
| | | 7 | 78 | 40 | 30 | 37.5 |
| | | 9 | 65 | 40 | 30 | 37.5 |
| | | Without BHI & NZ-CaseTT | | | | |
| HY-Soy | 22.75 | 7 | 82 | 40 | 30 | 37.5 |
| | 22.75 | 9 | 73 | 40 | 30 | 37.5 |
| | | With HY-Soy and without BHI & NZ-CaseTT | | | | |
| Hy-Yest | 7.5 | 9 | — | — | — | — |
| 412 | 15.0 | 7 | — | — | — | — |

TABLE 18-continued

| BHI Replacment | (g/l) | Time (day) | Kf | Lf $Lf_{FF}$ | $Lf_F$ | $Lf_{toxin}$ |
|---|---|---|---|---|---|---|
| (Quest) | 30.0 | 5 | 150 | 10 | 20 | 12.5 |
| Hy-Yest | 7.5 | 9 | >260 | 20 | 10 | 17.5 |
| 441 | 15.0 | 7 | — | — | — | — |
| (Quest) | 30.0 | 5 | — | — | — | — |
| Hy-Yest | 7.5 | 9 | >260 | 20 | 10 | 17.5 |
| 455 | 15.0 | 7 | — | — | — | — |
| (Quest) | 30.0 | 5 | — | — | — | — |

As in Table 17, HY-Soy could replace both BHI and NZ-CaseTT for toxin production. However, as also determined in Table 17, yeast extracts were inhibitory to toxin production. Therefore, the experiments outlined in Example 8 showed that Hy-Soy can replace both BHI and NZ-CaseTT in media for growth and for production of Tetanus Toxin by *C. tetani*. Furthermore, addition of yeast extracts to this medium interfered with Tetanus Toxin production.

Example 9

The purpose of experiments summarized in Tables 19–22 was to determine the effects of increasing the concentration of Hy-Soy from the concentration (22.75 g/L) used in Examples 3–6 in media lacking BHI and NZ-CaseTT for growth and production of Tetanus Toxin by *C. tetani*.

TABLE 19

| BHI Replacement | g/l | Growth ($OD_{660}$) 1(d) | 2(d) | 3(d) | 4(d) | 5(d) | 6(d) | 7(d) | 8(d) | 9(d) |
|---|---|---|---|---|---|---|---|---|---|---|
| | | | | Experiment 1 | | | | | | |
| | | | | With NZ-CaseTT | | | | | | |
| BHI | 22.75 | 0.46 | 0.65 | 0.80 | 0.73 | 0.33 | | | | |
| HY-Soy | 22.75 | 0.39 | 0.69 | 0.83 | 0.65 | 0.35 | | | | |

TABLE 19-continued

| BHI Replacement | g/l | \multicolumn{9}{c}{Growth (OD$_{660}$)} |
| --- | --- | --- | --- | --- | --- | --- | --- | --- | --- | --- |
| | | 1(d) | 2(d) | 3(d) | 4(d) | 5(d) | 6(d) | 7(d) | 8(d) | 9(d) |
| \multicolumn{11}{c}{Without BHI & NZ-CaseTT} |
| HY-Soy | 22.75 | 0.20 | 0.34 | 0.46 | 0.56 | 0.55 | 0.33 | 0.27 | | |
| | 34.13 | 0.25 | 0.45 | 0.66 | 0.73 | 0.75 | 0.58 | 0.48 | | |
| | 45.50 | 0.30 | 0.53 | 0.77 | 0.85 | 0.77 | 0.75 | 0.78 | | |
| | 56.88 | 0.35 | 0.60 | 0.93 | 0.85 | 0.89 | 1.02 | 1.03 | | |
| \multicolumn{11}{c}{Experiment 2} |
| \multicolumn{11}{c}{With NZ-CaseTT} |
| BHI | 22.75 | 0.42 | 0.64 | 0.84 | 0.72 | 0.35 | 0.26 | 0.28 | 0.30 | 0.29 |
| HY-Soy | 22.75 | 0.39 | 0.65 | 0.94 | 0.85 | 0.69 | 0.47 | 0.38 | 0.29 | 0.31 |
| \multicolumn{11}{c}{Without BHI & NZ-CaseTT} |
| HY-Soy | 22.75 | 0.17 | 0.34 | 0.49 | 0.56 | 0.58 | 0.38 | 0.31 | 0.27 | 0.26 |
| | 34.13 | 0.24 | 0.43 | 0.67 | 0.73 | 0.64 | 0.50 | 0.47 | 0.54 | 0.46 |

The initial OD$_{660}$ was <0.01.

The above data covering 2 experiments show that concentrations of HY-Soy greater than 22.75 indeed replaced both BHI and NZ-CaseTT. The concentration of Hy-Soy resulting in maximal growth of *C. tetani* was 56.88 g/L.

Table 20 summarizes the data on the production of Tetanus Toxin by *C. tetani* in fermentation media containing varying concentrations of Hy-Soy with and without BHI and NZ-CaseTT.

TABLE 20

| BHI | | | | Lf | | |
|---|---|---|---|---|---|---|
| Replacement | g/l | Time (d) | Kf | $Lf_{FF}$ | $Lf_F$ | $Lf_{toxin}$ |
| | | Experiment 1 | | | | |
| | | With NZ-CaseTT | | | | |
| BHI | 22.75 | 5 | 70 | 30 | 20 | 27.5 |
| HY-Soy | 22.75 | 5 | 80 | 40 | 30 | 37.5 |
| | | Without BHI & NZ-CaseTT | | | | |
| HY-Soy | 22.75 | 7 | 60 | 40 | 30 | 37.5 |
| | 34.13 | 7 | 60 | 40 | 50 | 42.5 |
| | 45.50 | 7 | >180 | 30 | 20 | 27.5 |
| | 56.88 | 7 | >180 | 30 | 20 | 27.5 |
| | | Experiment 2 | | | | |
| | | With NZ-CaseTT | | | | |
| BHI | 22.75 | 5 | 75 | 30 | 20 | 22.5 |
| | | 7 | 60 | 30 | 40 | 32.5 |
| | | 9 | 54 | 30 | 40 | 32.5 |
| HY-Soy | 22.75 | 5 | 90 | 30 | 20 | 27.5 |
| | | 7 | 78 | 40 | 30 | 37.5 |
| | | 9 | 65 | 40 | 30 | 37.5 |
| | | Without BHI & NZ-caseTT | | | | |
| HY-Soy | 22.75 | 7 | 82 | 40 | 30 | 37.5 |
| | | 9 | 73 | 40 | 30 | 37.5 |
| | 34.13 | 7 | 62 | 50 | 40 | 47.5 |
| | | 9 | 61 | 50 | 40 | 47.5 |

The above data confirm that HY-Soy at 22.75 g/l completely replaced both BHI and HY-CaseTT for toxin production. Unlike the effect on growth where 56.88 g/l HY-Soy was best, 34.13 g/l HY-Soy was best for toxin production. However this could be due to the fact that cells from 45.5 and 56.88 g/l HY-Soy had not lyzed by the end of the experiment.

TABLE 21

Summary of important results dealing with cell growth and Tetanus Toxin production in different media Cell growth:

| | Growth (OD660) | | | | | | | | |
|---|---|---|---|---|---|---|---|---|---|
| Media | 1(d) | 2(d) | 3(d) | 4(d) | 5(d) | 6(d) | 7(d) | 8(d) | 9(d) |
| | Control (BHI + NZ-CaseTT) | | | | | | | | |
| | 0.47 | 0.67 | 0.92 | 0.55 | 0.38 | | | | |
| | 0.38 | 0.61 | 0.81 | 0.70 | 0.31 | | | | |
| | 0.45 | 0.63 | 0.71 | 0.53 | 0.39 | | | | |
| | 0.43 | 0.62 | 0.85 | 0.56 | 0.31 | | | | |
| | 0.46 | 0.65 | 0.80 | 0.73 | 0.33 | | | | |
| | 0.42 | 0.64 | 0.84 | 0.72 | 0.35 | 0.26 | 0.28 | 0.30 | 0.29 |
| Ave | 0.44 | 0.64 | 0.82 | 0.63 | 0.35 | 0.26 | 0.28 | 0.30 | 0.29 |
| | HY-Soy with NZ-CaseTT & without BHI | | | | | | | | |
| | 0.45 | 0.77 | 0.94 | 0.54 | 0.37 | | | | |
| | 0.40 | 0.71 | 0.94 | 0.79 | 0.45 | | | | |
| | 0.39 | 0.69 | 0.83 | 0.65 | 0.35 | | | | |
| | 0.39 | 0.65 | 0.94 | 0.85 | 0.69 | 0.47 | 0.38 | 0.29 | 0.31 |
| Ave | 0.41 | 0.71 | 0.91 | 0.71 | 0.47 | 0.47 | 0.38 | 0.29 | 0.31 |
| | HY-Soy without BHI & NZ-CaseTT | | | | | | | | |
| 22.57 | 0.16 | 0.27 | 0.35 | 0.45 | 0.50 | | | | |
| g/l | 0.20 | 0.34 | 0.46 | 0.56 | 0.55 | 0.33 | 0.27 | | |
| | 0.17 | 0.34 | 0.49 | 0.56 | 0.58 | 0.38 | 0.31 | 0.27 | 0.26 |
| Ave | 0.18 | 0.32 | 0.43 | 0.52 | 0.54 | 0.36 | 0.29 | 0.27 | 0.26 |
| 34.13 | 0.25 | 0.45 | 0.66 | 0.73 | 0.75 | 0.58 | 0.48 | | |
| g/l | 0.24 | 0.43 | 0.67 | 0.73 | 0.64 | 0.50 | 0.47 | 0.54 | 0.46 |
| Ave | 0.25 | 0.44 | 0.67 | 0.73 | 0.70 | 0.54 | 0.48 | 0.54 | 0.46 |

*Each set of data represents a different experiment and each data point is the average of 3 tubes

TABLE 22

Production of Tetanus Toxin

| Media | Time (day) | Kf | LfFF | Lf LfF | Lftoxin |
|---|---|---|---|---|---|
| | Control (BHI + Nz-CaseTT) | | | | |
| | 5 | 60 | 30 | 20 | 27.5 |

TABLE 22-continued Production of Tetanus Toxin

| Media | Time (day) | Kf | LfFF | Lf LfF | Lftoxin |
|---|---|---|---|---|---|
| | 5 | 60 | 30 | 20 | 27.5 |
| | 5 | 70 | 30 | 20 | 27.5 |
| | 5 | 75 | 30 | 30 | 22.5 |
| | 7 | 60 | 30 | 40 | 32.5 |
| | 9 | 54 | 30 | 40 | 32.5 |
| HY-Soy with Nz-CaseTT & without BHI | | | | | |
| | 5 | 50 | 50 | 60 | 52.5 |
| | 5 | 80 | 40 | 30 | 37.5 |
| | 5 | 80 | 40 | 30 | 37.5 |
| | 5 | 90 | 30 | 20 | 27.5 |
| | 7 | 78 | 40 | 30 | 37.5 |
| | 9 | 65 | 40 | 30 | 37.5 |
| HY-Soy without BHI & Nz-CaseTT | | | | | |
| 22.75 g/l | 7 | 60 | 40 | 30 | 37.5 |
| | 9 | 65 | 40 | 30 | 37.5 |
| | 7 | 82 | 40 | 30 | 37.5 |
| | 9 | 73 | 40 | 30 | 37.5 |
| 34.13 g/l | 7 | 60 | 40 | 50 | 42:5 |
| | 9 | 75 | 30 | 40 | 32,5 |
| | 7 | 62 | 50 | 40 | 47.5 |
| | 9 | 61 | 50 | 40 | 47.5 |

Example 10

The purpose of experiments summarized in Example 10 was to determine if Hy-Soy or [Hy-Soy+Hy-Yest] can replace BHI and Bacto-peptone in media for seed growth of *C. tetani*. In addition, experiments in Example 10 were designed to determine the optimum concentrations of components in seed media to produce the maximum levels of Tetanus Toxin by *C. tetani*.

As indicated below in Tables 23–25, growth of *C. tetani* in seed media and in fermentation media containing Hy-Soy only (lacking BHI and Bacto-peptone) reaches levels similar to those attained for growth in media containing BHI. For a comparison, see Table 24; Fermentation nitrogen source: Hy-Soy only; row B (100 g Hy-Soy in seed medium) versus Fermentation nitrogen source: BHI+NZ-CaseTT; rows A–D.

TABLE 23

Seed growth*

| Nitrogen source of seed medium (per liter) | Growth (OD 660 nm) Stage 1 | Growth (OD 660 nm) Stage 2 |
|---|---|---|
| A 1000 mL BHI + 10 g Bacto-peptone | 0.14 | 0.32 |
| B 100 g Hy-Soy | 0.07 | 0.52 (48 h) |
| C 50 Hy-Soy | 0.07 | 0.22 |
| D 50 g Hy-Soy + 50 g Hy-Yest | 0.12 | 0.66 |

*Optical Density was measured after 24 hours unless indicated otherwise.

TABLE 24

Growth in fermentation media inoculated with seed cultures (A–D)

| Seed medium | Growth (OD 660 nm)* | | | | | | | | |
|---|---|---|---|---|---|---|---|---|---|
| | 1 d | 2 d | 3 d | 4 d | 5 d | 6 d | 7 d | 8 d | 9 d |
| Fermentation nitrogen source: NZ-case TT (15 g/l) + BHI (250 mL/L) | | | | | | | | | |
| A | 0.41 | 0.67 | 0.86 | 0.41 | 0.22 | 0.20 | 0.20 | 0.20 | 0.19 |

TABLE 24-continued

Growth in fermentation media inoculated with seed cultures (A–D)

| Seed medium | Growth (OD 660 nm)* | | | | | | | | |
|---|---|---|---|---|---|---|---|---|---|
| | 1 d | 2 d | 3 d | 4 d | 5 d | 6 d | 7 d | 8 d | 9 d |
| B | 0.45 | 0.71 | 0.97 | 0.91 | 0.31 | 0.23 | 0.25 | 0.25 | 0.23 |
| C | 0.43 | 0.68 | 0.85 | 0.21 | 0.22 | 0.27 | 0.33 | 0.32 | 0.21 |
| D | 0.41 | 0.65 | 0.85 | 0.41 | 0.26 | 0.24 | 0.21 | 0.20 | 0.19 |
| Fermentation nitrogen source: NZ-case TT (15 g/l) + HY-Soy (22.75 g/l) | | | | | | | | | |
| A | 0.39 | 0.69 | 0.91 | 0.73 | 0.46 | 0.35 | 0.31 | 0.31 | 0.28 |
| B | 0.45 | 0.75 | 1.00 | 0.87 | 0.52 | 0.39 | 0.33 | 0.33 | 0.33 |
| C | 0.40 | 0.67 | 0.64 | 0.32 | 0.28 | 0.27 | 0.27 | 0.28 | 0.25 |
| D | 0.42 | 0.72 | 0.96 | 0.74 | 0.45 | 0.39 | 0.37 | 0.37 | 0.35 |
| Fermentation nitrogen source: HY-Soy (35 g/l) only. | | | | | | | | | |
| A | 0.25 | 0.49 | 0.72 | 0.89 | 0.73 | 0.55 | 0.49 | 0.48 | 0.44 |
| B | 0.30 | 0.54 | 0.80 | 0.89 | 0.69 | 0.53 | 0.45 | 0.41 | 0.44 |
| C | 0.25 | 0.47 | 0.68 | 0.41 | 0.38 | 0.37 | 0.36 | 0.36 | 0.36 |
| D | 0.26 | 0.52 | 0.77 | 0.88 | 0.59 | 0.53 | 0.51 | 0.49 | 0.46 |

*Before fermentation, the OD 660 nm was 0.

Table 25 indicates that toxin production by *C. tetani* grown in seed medium and fermentation medium that is free of BHI and NZ-CaseTT reached (or exceeded) levels attained in media containing BHI and NZ-CaseTT. For a comparison, see Fermentation nitrogen source: Hy-Soy; row B and C; day 9 (Lf toxin=57.5) versus Fermentation nitrogen source NZ-CaseTT+BHI row A–D (Lf toxin=47.5).

TABLE 25

Toxin production with different seed cultures:

| Seed medium | Kf | | | Lftoxin | | |
|---|---|---|---|---|---|---|
| | 5 d | 7 d | 9 d | 5 d | 7 d | 9 d |
| Fermentation nitrogen source: NZ-case TT 15 g/l + BHI 250 ml/l | | | | | | |
| A | 63 | 60 | 52 | 37.5 | 37.5 | 42.5 |
| B | 66 | 52 | 51 | 42.5 | 47.5 | 42.5 |
| C | 76 | 60 | 52 | 32.5 | 32.5 | 32.5 |
| D | 70 | 65 | 51 | 32.5 | 37.5 | 32.5 |
| Fermentation nitrogen source: NZ-case TT 15 g/l + HY-Soy 22.75 g/l | | | | | | |
| A | 83 | 70 | 56 | 32.5 | 42.5 | 37.5 |
| B | 117 | 60 | 60 | 27.5 | 37.5 | 37.5 |
| C | 92 | 97 | 81 | 27.5 | 27.5 | 22.5 |
| D | 73 | 59 | 48 | 32.5 | 37.5 | 37.5 |
| Fermentation nitrogen source: HY-Soy 35 g/l | | | | | | |
| A | — | 56 | 44 | — | 52.5 | 57.5 |
| B | — | 51 | 49 | — | 52.5 | 57.5 |
| C | 65 | 57 | 51 | 42.5 | 47.5 | 57.5 |
| D | — | 57 | 43 | — | 52.5 | 57.5 |

Tables 23–25 show that Hy-Soy or [Hy-Soy+Hy-Yest] can replace both BHI and Bacto-peptone for seed growth. In addition, the seed culture of Hy-Soy or [Hy-Soy+Hy-Yest] supported excellent cell growth and toxin production in different fermentation media including fermentation media free of BHI and NZ-CaseTT. The optimal concentrations of Hy-Soy in the seed and fermentation media were assayed in the following examples and range from approximately 50–150 g/L Hy-Soy in the seed medium and 15–50 g/L Hy-Soy in the fermentation medium for both growth and for Tetanus Toxin production.

Example 11

The purpose of experiments summarized in Example 11 was to determine the optimum concentrations of Hy-Soy or

[Hy-Soy+Hy-Yest] for growth in the seed medium (Table 26). In addition, the effects of different Hy-Soy or [Hy-Soy+Hy-Yest] in the seed medium on growth (Table 27) and Tetanus Toxin production (Table 28) in the fermentation stage were tested.

TABLE 26

Seed growth

| Nitrogen source of seed medium (per liter) | Growth (OD 660 nm) | | |
|---|---|---|---|
| | Step-1 seed | Step-2 seed | |
| | 24 h | 24 h | 48 h |
| A BHI 1000 ml + Bacto-peptone 10 g | 0.12 | 0.33 | 0.30 |
| B1 Hy-Soy 50 g | 0.03 | 0.14 | 0.36 |
| B2 Hy-Soy 62.5 g | 0.02 | 0.01 | 0.32 |
| B3 Hy-Soy 75 g | 0.03 | 0.02 | 0.41 |
| B4 Hy-Soy 87.5 g | 0.03 | 0.09 | 0.51 |
| B5 Hy-Soy 100 g | 0.02 | 0.00 | 0.38 |
| C1 Hy-Soy 50 g + Hy-Yest 10 g | 0.04 | 0.25 | 0.36 |
| C2 Hy-Soy 50 g + Hy-Yest 20 g | 0.07 | 0.47 | 0.41 |
| C3 Hy-Soy 50 g + Hy-Yest 30 g | 0.02 | 0.53 | 0.41 |
| C4 Hy-Soy 50 g + Hy-Yest 40 g | 0.02 | 0.56 | 0.42 |
| C5 Hy-Soy 50 g + Hy-Yest 50 g | 0.02 | .027 | .064 |

TABLE 27

Growth in Hy-Soy fermentation medium inoculated with different seed cultures

| Seed medium | Growth (OD 660 nm)* | | | | | | | | |
|---|---|---|---|---|---|---|---|---|---|
| | 1 d | 2 d | 3 d | 4 d | 5 d | 6 d | 7 d | 8 d | 9 d |
| A | 0.06 | 0.26 | 0.41 | 0.65 | 0.63 | 0.41 | 0.36 | 0.31 | 0.26 |
| B1 | 0.27 | 0.48 | 0.67 | 0.32 | 0.24 | 0.22 | 0.21 | 0.20 | 0.17 |
| B2 | 0.27 | 0.44 | 0.57 | 0.73 | 0.70 | 0.57 | 0.38 | 0.32 | 0.29 |
| B3 | 0.28 | 0.45 | 0.63 | 0.39 | 0.23 | 0.22 | 0.18 | 0.18 | 0.17 |
| B4 | 0.30 | 0.47 | 0.12 | 0.14 | 0.13 | 0.14 | 0.14 | 0.14 | 0.14 |
| B5 | 0.26 | 0.36 | 0.48 | 0.60 | 0.52 | 0.37 | 0.27 | 0.24 | 0.21 |
| C1 | 0.24 | 0.40 | 0.59 | 0.67 | 0.45 | 0.31 | 0.26 | 0.22 | 0.18 |
| C2 | 0.20 | 0.36 | 0.58 | 0.63 | 0.39 | 0.33 | 0.29 | 0.25 | 0.23 |
| C3 | 0.24 | 0.41 | 0.61 | 0.57 | 0.37 | 0.31 | 0.28 | 0.25 | 0.23 |
| C4 | 0.25 | 0.41 | 0.60 | 0.56 | 0.35 | 0.29 | 0.27 | 0.23 | 0.21 |
| C5 | 0.15 | 0.30 | 0.44 | 0.59 | 0.49 | 0.36 | 0.31 | 0.27 | 0.24 |

*Before fermentation, the OD 660 nm was 0.

TABLE 28

Toxin production with different seed cultures

| Seed medium | Kf | | | Lftoxin | | |
|---|---|---|---|---|---|---|
| | 5 d | 7 d | 9 d | 5 d | 7 d | 9 d |
| A | — | 86 | 70 | — | 32.5 | 27.5 |
| B1 | 69 | 61 | 60 | 37.5 | 42.5 | 42.5 |
| B2 | — | 62 | 48 | — | 42.5 | 47.5 |
| B3 | — | 60 | 60 | — | 47.5 | 42.5 |
| B4 | >180 | >180 | >180 | 22.5 | 22.5 | 22.5 |
| B5 | — | 62 | 40 | — | 42.5 | 47.5 |
| C1 | — | 99 | 92 | — | 22.5 | 17.5 |
| C2 | — | 91 | 94 | — | 27.5 | 17.5 |
| C3 | — | 94 | 92 | — | 37.5 | 27.5 |
| C4 | — | 91 | 92 | — | 32.5 | 17.5 |
| C5 | — | 93 | 94 | — | 27.5 | 17.5 |

The experiments summarized in Tables 26–28 confirm that Hy-Soy can replace BHI and Bacto-peptone as the nitrogen source in seed medium for growth of *C. tetani* and for production of Tetanus Toxin in the subsequent fermentation phase. Also, Hy-Soy as nitrogen source in the seed medium, as compared to Hy-Soy plus Hy-Yest, produced higher levels of Tetanus Toxin in the subsequent fermentation step. The concentrations of Hy-Soy in seed medium that produce the best levels of toxin range from approximately 62.5 g/L to 100 g/L.

Tables 29–30 summarize additional experiments designed to determine the optimum concentrations of Hy-Soy in the seed medium for the maximum production of Tetanus Toxin by *C. tetani* by fermentation. As shown in Table 30, 50 g, 75 g and 100 g of Hy-Soy in the seed medium all resulted in production of Tetanus Toxin by fermentation of *C. tetani* that is comparable or exceeds levels of Tetanus Toxin production in seed medium containing BHI and Bacto-peptone as a nitrogen source.

TABLE 29

Seed growth

| Nitrogen source of seed medium (per liter) | Growth (OD 660 nm) | | |
|---|---|---|---|
| | Step-1 seed | Step-2 seed | |
| | 24 h | 48 h | 48 h |
| 1000 ml BHI + 10 g peptone | 0.15 | 0.40 | 0.30 |
| 50 g Hy-Soy | 0.035 | 0.10 | 0.29 |
| 75 g Hy-Soy | 0.01 | 0.18 | 0.38 |
| 100 g Hy-Soy | 0.03 | 0.25 | 0.51 |

TABLE 30

Growth in Hy-Soy fermentation media inoculated with different seed cultures:

| Seed medium N source (per liter) | Growth (OD 660 nm)* | | | | | | |
|---|---|---|---|---|---|---|---|
| | 1 d | 2 d | 3 d | 4 d | 5 d | 6 d | 7 d |
| 1000 ml BHI + 10 g peptone | 0.19 | 0.37 | 0.58 | 0.79 | 0.69 | 0.45 | 0.41 |
| 50 g Hy-Soy | 0.15 | 0.32 | 0.56 | 0.74 | 0.63 | 0.49 | 0.39 |
| 75 g Hy-Soy | 0.19 | 0.35 | 0.60 | 0.77 | 0.68 | 0.49 | 0.45 |
| 100 g Hy-Soy | 0.22 | 0.41 | 0.63 | 0.38 | 0.25 | 0.24 | 0.23 |

*Before fermentation, the OD 660 nm was 0.

TABLE 31

Toxin production with different seed cultures (7 days)

| Seed medium N Source (per liter) | Kf | Lftoxin |
|---|---|---|
| 1000 ml BHI + 10 g peptone | 150 | 32.5 |
| 50 g Hy-Soy | 150 | 47.5 |
| 75 g Hy-Soy | 155 | 37.5 |
| 100 g Hy-Soy | 58 | 57.5 |

The data in Tables 26–31 indicate that a concentration of 100 g/L Hy-Soy in the seed medium resulted in the highest levels of toxin production in the subsequent fermentation step. In addition, the data indicate that seed step-1 of Hy-Soy seed medium produced greater growth after 48 hours than after 24 hours.

Example 12

The three experiments summarized in Tables 32–34 were designed to determine the optimum concentration of the second stage seed growth containing *C. tetani* and the optimum length of time for the second stage seed growth that will produce that highest levels of Tetanus Toxin.

TABLE 32

Growth of second stage seed culture

| Expt. | 1 d | 2 d | 3 d | 4 d | 5 d | 6 d |
|---|---|---|---|---|---|---|
| | | | OD 660 nm | | | |
| A | 0.38 | 0.60 | 0.87 | 0.95 | 0.41 | 0.34 |
| B | 0.31 | 0.61 | 0.90 | — | — | — |
| C | 0.46 | 0.77 | 1.03 | — | — | — |

TABLE 33

Growth of production culture

| | 1 d | 2 d | 3 d | 4 d | 5 d | 6 d | 7 d |
|---|---|---|---|---|---|---|---|
| | | | Growth (OD 660 nm) | | | | |
| Expt./Age of 2nd seed | | | | | | | |
| A/1 d | 0.20 | 0.39 | 0.61 | 0.77 | 0.74 | 0.57 | 0.40 |
| A/2 d | 0.23 | 0.43 | 0.67 | 0.79 | 0.71 | 0.49 | 0.38 |
| A/3 d | 0.25 | 0.44 | 0.69 | 0.82 | 0.66 | 0.45 | 0.38 |
| A/4 d | 0.21 | 0.40 | 0.68 | 0.83 | 0.72 | 0.48 | 0.36 |
| A/5 d | 0.19 | 0.34 | 0.57 | 0.77 | 0.78 | 0.55 | 0.40 |
| A/6 d | 0.16 | 0.28 | 0.45 | 0.61 | 0.75 | 0.68 | 0.51 |
| B/1 d | 0.22 | 0.42 | 0.59 | 0.73 | 0.66 | 0.47 | 0.40 |
| B/2 d | 0.21 | 0.38 | 0.66 | 0.75 | 0.70 | 0.55 | 0.44 |
| B/3 d | 0.21 | 0.42 | 0.68 | 0.78 | 0.66 | 0.47 | 0.39 |
| C/1 d | 0.23 | 0.47 | 0.75 | 0.87 | 0.78 | 0.61 | 0.49 |
| C/2 d | 0.21 | 0.47 | 0.75 | 0.85 | 0.75 | 0.55 | 0.41 |
| C/3 d | 0.24 | 0.48 | 0.77 | 0.86 | 0.74 | 0.55 | 0.42 |
| Expt./Inoculum conc (%)* | | | | | | | |
| C/0.25 | 0.21 | 0.45 | 0.72 | 0.86 | 0.77 | 0.61 | 0.47 |
| C/0.5 | 0.23 | 0.47 | 0.75 | 0.87 | 0.78 | 0.61 | 0.49 |
| C/1.0 | 0.24 | 0.51 | 0.79 | 0.86 | 0.74 | 0.59 | 0.45 |
| C/2.0 | 0.27 | 0.54 | 0.80 | 0.86 | 0.73 | 0.58 | 0.44 |
| C/4.0 | 0.30 | 0.56 | 0.84 | 0.85 | 0.71 | 0.51 | 0.40 |

*The inoculum was a 24 h second stage seed culture.

TABLE 34

Toxin production (after 7 days of fermentation)

| Expt./Age of seed (d) | Kf | Lftoxin |
|---|---|---|
| A/1 d | 61 | 52.5 |
| A/2 d | 65 | 52.5 |
| A/3 d | 52 | 57.5 |
| A/4 d | 49 | 52.5 |
| A/5 d | 58 | 47.5 |
| A/6 d | 113 | 37.5 |
| B/1 d | 71 | 37.5 |
| B/2 d | 71 | 42.5 |
| B/3 d | 66 | 47.5 |
| C/1 d | 68 | 37.5 |
| C/2 d | 65 | 52.5 |
| C/3 d | 58 | 57.5 |

| Expt./Inoculum (%) | Kf | Lftoxin |
|---|---|---|
| C/0.25 | 63 | 37.5 |
| C/0.5 | 68 | 37.5 |
| C/1.0 | 73 | 47.5 |
| C/2.0 | 59 | 52.5 |
| C/4.0 | 61 | 52.5 |

The above data show that (i) the age of the second stage seed culture of 1 to 4 days supports for growth and production; (ii) 5 and 6 day seed cultures were poor; at 5–6 days, the seed culture has begun to lyze. (iii) Growth of the second stage seed for 3 days appeared optimal for production. (iv) Use of 2% and 4% second stage seed culture as inoculum appeared optimal for toxin production.

Example 13

Experiments summarized in this Example were designed to examine the effects of different iron concentrations in fermentation medium for growth of C. tetani. In addition, the effects of sterilizing iron alone or with the medium were examined.

TABLE 35

Basal Fermentation medium

| Components | Medium composition (g/L) | | | |
|---|---|---|---|---|
| Glucose | 7.5 | | | |
| Hy-Soy | 35.0 | | | |
| L-Cysteine | 0.125 | | | |
| L-Tyrosine | 0.125 | | | |
| NaCl | 5.0 | | | |
| $Na_2HPO_4$ | 0.5 | | | |
| $MgSO_4$ | 0.05 | | | |
| $KH_2PO_4$ | 0.175 | | | |
| Variations | Fermentation Media | | | |
| Iron autoclaved separately | C1 | C2 | C3 | C4 |
| Iron autoclaved with medium | MC1 | MC2 | MC3 | MC4 |
| Concentration of powdered iron (g/L) | 0.25 | 0.5 | 1.0 | 2.0 |

Initial pH = 6.8

Growth in Fermentation Media:

TABLE 38

| Medium | 1 d | 2 d | 3 d | 4 d | 5 d | 6 d | 7 d | 8 d | 9 d |
|---|---|---|---|---|---|---|---|---|---|
| | | | | Growth (OD 660 nm)* | | | | | |
| C1 | 0.21 | 0.41 | 0.55 | 0.70 | 0.63 | 0.49 | 0.39 | 0.32 | 0.29 |
| C2 (control) | 0.22 | 0.42 | 0.59 | 0.73 | 0.66 | 0.47 | 0.40 | 0.35 | 0.31 |
| C3 | 0.20 | 0.45 | 0.66 | 0.79 | 0.68 | 0.50 | 0.45 | 0.39 | 0.35 |
| C4 | 0.19 | 0.39 | 0.64 | 0.79 | 0.67 | 0.50 | 0.45 | 0.39 | 0.36 |
| MC1 | 0.49 | 0.72 | 0.96 | 1.00 | 0.72 | 0.48 | 0.33 | 0.31 | 0.38 |
| MC2 (control) | 0.77 | 0.90 | 1.15 | 1.20 | 0.86 | 0.67 | 0.46 | 0.46 | 0.42 |
| MC3 | 0.92 | 1.30 | 1.20 | 1.10 | 0.94 | 0.79 | 0.69 | 0.59 | 0.56 |
| MC4 | 1.30 | 1.45 | 1.40 | 1.08 | 0.66 | 0.45 | 0.35 | 0.30 | 0.32 |

*Before fermentation, the OD 660 nm was 0.

TABLE 39

Toxin production

| Medium | Kf | | Lftoxin | |
|---|---|---|---|---|
| | 7d | 9d | 7d | 9d |
| C1 | 87 | 79 | 32.5 | 47.5 |
| C2 (control) | 78 | 68 | 37.5 | 47.5 |
| C3 | 72 | 70 | 42.5 | 47.5 |
| C4 | 66 | 71 | 42.5 | 47.5 |
| MC1 | 54 | 40 | 52.5 | 67.5 |
| MC2 (control) | 76 | 48 | 32.5 | 47.5 |
| MC3 | 85 | 68 | 27.5 | 37.5 |
| MC4 | 104 | 83 | 17.5 | 32.5 |

The data summarized in Tables 35–39 show that MC1 medium containing 0.25 g of iron per L of the control medium autoclaved together with the medium resulted in the highest levels of Tetanus Toxin production. This medium differed from control medium (MC2) only by the amount of powdered iron. The control MC2 medium contained twice as much powdered iron as MC1. For both media, the iron was autoclaved together with the other components. Thus, the concentration of powdered iron was a major factor influencing toxin production when the powdered iron was autoclaved with other components in the medium. Medium containing 0.25 g/L of powdered iron produced the highest levels of toxin, and medium containing 2 g/L of powdered iron produced the lowest levels. Iron concentration did not affect the levels of toxin production when the iron was autoclaved separately from the rest of the media.

Example 14

Experiments described in this example were designed to study the effect of different methods of media sterilization on toxin production. More specifically, the methods for sterilization of glucose in seed and fermentation media containing Hy-Soy were examined.

The three method of sterilization were as follows:

A. All components autoclaved together (standard procedure).
B. Glucose autoclaved separately.
C. Glucose sterilized by filtration with<0.2 μm filter.

TABLE 40

Seed growth:

| Sterilization of glucose for seed | Step-1 | Step-2 | | | | | |
|---|---|---|---|---|---|---|---|
| | 2 d | 1 d | 2 d | 3 d | 4 d | 5 d | 6 d |
| A | 0.24 | 0.31 | 0.60 | 0.85 | 0.88 | 0.75 | 0.71 |
| B | 0.11 | 0.06 | 0.55 | 0.91 | 1.08 | 0.89 | 0.68 |
| C | 0.10 | <0.01 | 0.45 | 0.63 | 0.85 | 0.98 | 0.91 |

TABLE 41

Effects of different methods of sterilization of seed media on growth in fermentation medium

| Sterilization of glucose for fermentation medium | Growth (OD 660 nm)* | | | | | | |
|---|---|---|---|---|---|---|---|
| | 1 d | 2 d | 3 d | 4 d | 5 d | 6 d | 7 d |
| All components of seed medium autoclaved together | | | | | | | |
| A | 0.22 | 0.41 | 0.57 | 0.73 | 0.44 | 0.27 | 0.24 |
| B | 0.32 | 0.50 | 0.73 | 0.77 | 0.41 | 0.32 | 0.29 |
| C | 0.35 | 0.53 | 0.72 | 0.81 | 0.43 | 0.33 | 0.29 |
| Glucose autoclaved separately in seed medium | | | | | | | |
| A | 0.24 | 0.43 | 0.63 | 0.68 | 0.31 | 0.24 | 0.21 |
| B | 0.35 | 0.54 | 0.78 | 0.75 | 0.38 | 0.32 | 0.25 |
| C | 0.33 | 0.50 | 0.76 | 0.73 | 0.37 | 0.30 | 0.25 |
| Glucose sterilized by filtration with <0.2 μm filter for seed medium | | | | | | | |
| A | 0.21 | 0.38 | 0.60 | 0.74 | 0.62 | 0.40 | 0.34 |
| B | 0.36 | 0.49 | 0.71 | 0.84 | 0.63 | 0.41 | 0.31 |
| C | 0.34 | 0.48 | 0.69 | 0.85 | 0.63 | 0.42 | 0.35 |

*Before fermentation, the OD 660 nm was 0.

TABLE 42

Effects on different methods of sterilization of seed media on toxin production (7 days)

| Sterilization of glucose for fermentation medium | Kf | Lftoxin |
|---|---|---|
| All components of seed medium autoclaved together | | |
| A | 61 | 47.5 |
| B | 79 | 40.0 |
| C | 77 | 42.5 |
| Glucose autoclaved separately in seed medium | | |
| A | 54 | 47.5 |
| B | 71 | 42.5 |
| C | 72 | 42.5 |
| Glucose sterilized by filtration with <0.2 μm filter for seed medium | | |
| A | 72 | 47.5 |
| B | 96 | 42.5 |
| C | 93 | 42.5 |

The results shown in Tables 40–42 demonstrated that *Clostridium tetani* grew faster in seed medium when glucose was autoclaved with the other components of the seed medium as compared to media containing glucose that was autoclaved separately or sterile-filtered separately. Also, Tetanus Toxin production was slightly higher in fermentation medium when glucose was autoclaved with the other fermentation medium components than when glucose was autoclaved separately or filtered separately. Thus, autoclaving glucose with the rest of the medium is beneficial for seed growth and toxin production in fermentation medium.

Example 15

Experiments in Example 15 were designed to determine the effects on growth and toxin production of adding growth factors of the Mueller and Miller (MM) medium to the fermentation medium containing Hy-Soy as the source of nitrogen. These growth factors include Ca-pantothenate, uracil, thiamine, riboflavin, pyridoxine, and biotin.

TABLE 43

Growth in fermentation media:

| Fermentation medium | Growth (OD 660 nm)* | | | | | | |
|---|---|---|---|---|---|---|---|
| | 1 d | 2 d | 3 d | 4 d | 5 d | 6 d | 7 d |
| Seed medium: 1000 ml BHI + 10 g/l Bacto-peptone | | | | | | | |
| Hy-Soy | 0.19 | 0.37 | 0.58 | 0.79 | 0.69 | 0.45 | 0.41 |
| Hy-Soy + growth factors** | 0.22 | 0.38 | 0.58 | 0.76 | 0.78 | 0.54 | 0.50 |
| Mueller & Miller | 0.44 | 0.70 | 0.76 | 0.80 | 0.44 | 0.32 | 0.30 |
| Seed medium: 100 g/l Hy-Soy | | | | | | | |
| Hy-Soy | 0.22 | 0.41 | 0.63 | 0.38 | 0.25 | 0.24 | 0.23 |
| Hy-Soy + growth factors | 0.24 | 0.43 | 0.61 | 0.73 | 0.32 | 0.29 | 0.27 |
| Mueller & Miller | 0.47 | 0.67 | 0.55 | 0.19 | 0.19 | 0.20 | 0.21 |

*Before fermentation, the OD 660 nm was 0.
**Growth factors are Ca-pantothenate, 1 mg/l; uracil, 2.5 mg/l; thiamine, 0.25 mg/l; riboflavin, 0.25 mg/l; pyridoxine, 0.25 mg/l; biotin, 2.5 μg/l

TABLE 44

Toxin production

| Fermentation medium | Kf 5 d | Kf 6 d | Kf 7 d | Lftoxin 5 d | Lftoxin 6 d | Lftoxin 7 d |
|---|---|---|---|---|---|---|
| Seed medium: 1000 ml BHI + 10 g/l Bacto-peptone | | | | | | |
| Hy-Soy | — | >180 | 150 | — | 27.5 | 32.5 |
| Hy-Soy + growth factors | — | | >180 | — | — | 17.5 |
| Mueller & Miller | — | 54 | 60 | — | 17.5 | 17.5 |
| Seed medium: 100 g/l Hy-Soy | | | | | | |
| Hy-Soy | 80 | 70 | 58 | 37.5 | 47.5 | 57.5 |
| Hy-Soy + growth factors | — | 76 | 59 | — | 47.5 | 57.5 |
| Mueller & Miller | 65 | 68 | 70 | 32.5 | 32.5 | 32.5 |

The results of experiments summarized in Table 43–44 demonstrate that growth factors of the Mueller and Miller medium added to medium containing Hy-Soy as the sole source of nitrogen may have a marginal effect on growth but did not improve toxin production in the Hy-Soy fermentation medium. The best production was observed with Hy-Soy seed in combination with Hy-Soy fermentation medium.

Example 16

Sources of Iron

Experiments in Example 19 were designed to examine the effect of various iron sources on the production of Tetanus Toxin. The results in Table 47 show that sources of iron such as ferrous sulfate, ferrous gluconate, ferric citrate and ferric nitrate were not able to replace powdered iron for production of toxin, although some toxin was produced with ferric citrate. However growth and production of toxin were observed for all iron sources except ferrous gluconate.

| Seed medium | (%) |
|---|---|
| Hy-Soy | 10.0 |
| NaCl | 0.5 |
| Glucose | 1.0 |
| pH | 8.1 |
| Fermentation medium: | |
| Basal medium without Fe: | |
| Hy-Soy | 35.0 g/l |
| Glucose | 7.5 g/l |
| NaCl | 5.0 g/l |
| $Na_2HPO_4$ | 0.5 g/l |
| $KH_2PO_4$ | 175 mg/l |
| $MgSO_4$—$7H_2O$ | 50 mg/l |
| L-cysteine | 125 mg/l |
| L-tyrosine | 125 mg/l |

TABLE 45

| Iron Components | Grams/Liter | | | |
|---|---|---|---|---|
| Powdered iron | 0.0625 | 0.125 | 0.25 | 0.50 |
| Ferrous sulfate ($FeSO_4$—$7H_2O$) | 0.625 | 1.25 | 2.50 | |
| Ferrous gluconate ($FeC_{12}H_{22}O_{14}$) | 1.075 | 2.15 | 4.30 | |
| Ferric citrate ($FeC_6H_5O_7$) | 0.55 | 1.10 | 2.20 | |
| Ferric nitrate ($Fe(NO_3)_3 \cdot 9H_2O$) | 0.90 | 1.30 | 3.60 | | pH 6.8

Method

As previously described, all media were prepared with double-distilled water. Iron-containing compounds listed in Table 45 were added to the fermentation medium lacking iron (basal medium). The final concentrations of ingredients in media are provided as grams/liter. The pH of the solutions were adjusted to 6.8 with 5 N NaOH. For purposes of sterilization, iron-containing compounds were autoclaved with the other ingredients of the media. Two stages of seed culture were used. The length of incubation for both seed cultures was approximately 48 hours. 2% of the second stage seed culture was used as an inoculum for the fermentation media. Table 47 indicates the levels of toxin production after 7 days and 9 days of fermentation for different sources of iron.

TABLE 46

Toxin production with different concentrations of powdered iron.

| Iron (g/l) | $K_f$ 7d | $K_f$ 9d | $L_f$toxin 7d | $L_f$toxin 9d |
|---|---|---|---|---|
| 0 | >180 | 45 | 12.5 | 22.5 |
| 0.0625 | 49 | 55 | 52.5 | 52.5 |
| 0.125 | 44 | 55 | 52.5 | 52.5 |
| 0.25 | 47 | 56 | 57.5 | 52.5 |
| 0.50 | 51 | 57 | 67.5 | 72.5 |

TABLE 47

Toxin production (on 7th day) with different concentrations of Fe components:

| Ferrous Sulfate (g/l) | $K_f$ | $L_f$toxin |
|---|---|---|
| 0.625 | >180 | 12.5 |
| 1.25 | >180 | 12.5 |
| 2.50 | >180 | <7.5 |
| Ferrous gluconate (g/l) | | |
| 1.075 | >180 | <7.5 |
| 2.15 | >180 | <7.5 |
| 4.30 | >180 | |
| Ferric citrate (g/l) | | |
| 0.55 | 160 | 22.5 |
| 1.10 | 165 | 17.5 |
| 2.20 | 165 | 17.5 |
| Ferric nitrate (g/l) | | |
| 0.90 | 170 | 17.5 |
| 1.80 | >180 | <7.5 |
| 3.60 | >180 | <7.5 |

Example 17

Storage of Cultures in Soy Milk

The purpose of experiments described in Example 17 was to determine the effects of using *C. tetani* cultures that were lyophilized and stored in soy milk at 4° C.

Microorganisms

*Clostridium tetani* (preparation 3-ABI-13; lyophilized culture of animal milk, stored at 4° C.).

*Clostridium tetani* (preparation SM-409-0998-1; lyophilized culture of soy-milk, stored at 4° C.).

| Seed medium (%): | |
|---|---|
| Hy-Soy | 10.0 |
| NaCl | 0.05 |
| Glucose | 1.0 |

-continued

| | |
|---|---|
| pH | 8.1 |

Fermentation medium:

| | |
|---|---|
| Hy-Soy | 35.0 g/l |
| Glucose | 7.5 g/l |
| NaCl | 5.0 g/l |
| $Na_2HPO_4$ | 0.5 g/l |
| $KH_2PO_4$ | 175 mg/l |
| $MgSO_4 \cdot 7H_2O$ | 50 mg/l |
| L-Cysteine | 125 mg/l |
| L-Tyrosine | 125 mg/l |
| Powdered iron | 0.5 g/l |
| pH | 5.6–7.4 |

Methods

1. Stage 1 and 2 seed cultures were both incubated for approximately 48 hours. The inoculum for the fermentation phase was 2% of second stage seed culture. Growth in seed media and fermentation were performed as previously described.

Results

TABLE 48

Seed culture with different lyophilized stock cultures:

| Lyophilized stock culture | Growth of Step-2 seed culture (OD 660 nm)* | | | | |
|---|---|---|---|---|---|
| | 1(d) | 2(d) | 3(d) | 4(d) | 5(d) |
| Animal Milk (3-ABI-13) | 0.51 | 0.81 | 0.96 | 0.43 | 0.33 |
| Soy Milk (SM-409-0998-1) | 0.59 | 0.90 | 0.88 | 0.43 | 0.38 |

*1 ml lyophilized stock culture into 10 ml of step-1 seed medium; 1 ml step-1 seed culture into 40 ml of step-2 seed medium in a 75 ml flask.

TABLE 49

Cell growth in fermentation medium

| Lyophilized stock culture | Growth (OD 660 nm) | | | | | | | |
|---|---|---|---|---|---|---|---|---|
| | 1(d) | 2(d) | 3(d) | 4(d) | 5(d) | 6(d) | 7(d) | 9(d) |
| Animal Milk | 0.37 | 0.62 | 0.79 | 0.78 | 0.49 | 0.34 | 0.30 | 0.27 |
| Soy Milk | 0.34 | 0.56 | 0.74 | 0.54 | 0.37 | 0.30 | 0.27 | 0.24 |

TABLE 50

Toxin Production

| | Kf | | $L_f$toxin | |
|---|---|---|---|---|
| | 7d | 9d | 7d | 9d |
| Animal Milk | 46 | 47 | 62.5 | 62.5 |
| Soy Milk | 49 | 49 | 52.5 | 57.5 |

The results of experiments summarized in Tables 48–50 show that cultures of *C. tetani* lyophilized and stored in soy milk lacking any animal milk can be used to inoculate a seed medium for subsequent growth and production of Tetanus Toxin. In addition, Tables 48–50 show that production of Tetanus Toxin by *C. tetani* originating from cultures stored in soymilk and grown in soy seed medium and soy fermentation medium was comparable to levels of Tetanus Toxin production by *C. tetani* derived from cultures stored in animal milk.

Example 18

The Effects of Initial pH on Growth and Toxin Production

The effects of initial pH on the growth of *C. tetani* and the production of Tetanus Toxin were examined. Table 51 shows that cell lysis (as measured by decreasing O.D.) varied according to the initial pH value of the medium. Generally, the degree of cell lysis decreased as the initial pH of the starting fermentation medium was increased. Table 52 shows that Tetanus Toxin production was highest when the initial pH of the fermentation medium was approximately 6.0–6.2.

TABLE 51

Cell growth in fermentation medium at different initial pH values.

| pH | Growth (OD 660 nm)* | | | | | | | |
|---|---|---|---|---|---|---|---|---|
| | 1(d) | 2(d) | 3(d) | 4(d) | 5(d) | 6(d) | 7(d) | 9(d) |
| 5.6 | 0.20 | 0.32 | 0.41 | 0.28 | 0.13 | 0.11 | 0.10 | 0.10 |
| 5.8 | 0.22 | 0.36 | 0.48 | 0.45 | 0.17 | 0.13 | 0.12 | 0.13 |
| 6.0 | 0.26 | 0.43 | 0.53 | 0.50 | 0.21 | 0.16 | 0.16 | 0.17 |
| 6.2 | 0.26 | 0.43 | 0.48 | 0.51 | 0.22 | 0.20 | 0.20 | 0.21 |
| 6.4 | 0.35 | 0.55 | 0.71 | 0.46 | 0.24 | 0.20 | 0.18 | 0.19 |
| 6.6 | 0.50 | 0.73 | 0.93 | 0.87 | 0.41 | 0.26 | 0.21 | 0.16 |
| 6.8** | 0.37 | 0.62 | 0.79 | 0.78 | 0.49 | 0.34 | 0.30 | 0.27 |
| 7.0 | 0.37 | 0.61 | 0.78 | 0.71 | 0.41 | 0.31 | 0.28 | 0.26 |
| 7.2 | 0.70 | 1.01 | 1.13 | 0.99 | 0.75 | 0.44 | 0.35 | 0.39 |
| 7.4 | 0.37 | 0.75 | 0.88 | 0.88 | 0.65 | 0.45 | 0.41 | 0.41 |

*OD of second stage seed culture at the time of inoculation of fermentation medium: Animal milk lyophilized culture = 0.97.
**Control

TABLE 52

Toxin production with different initial pH of fermentation medium

| | Kf | | $L_f$toxin | |
|---|---|---|---|---|
| pH | 7d | 9d | 7d | 9d |
| 5.6 | 49 | 46 | 57.5 | 62.5 |
| 5.8 | 40 | 43 | 62.5 | 62.5 |
| 6.0 | 40 | 41 | 67.5 | 67.5 |
| 6.2 | 40 | 41 | 67.5 | 67.5 |
| 6.4 | 42 | 50 | 57.5 | 57.5 |
| 6.6 | 63 | 51 | 52.5 | 47.5 |
| 6.8 | 46 | 47 | 62.5 | 62.5 |
| 7.0 | 57 | 43 | 57.5 | 52.5 |
| 7.2 | 103 | 61 | 27.5 | 32.5 |
| 7.4 | 83 | 54 | 32.5 | 32.5 |

TABLE 53

| | pH Measurements | | |
|---|---|---|---|
| pH | Before Autoclaving | After autoclaving | Final |
| 5.6 | 5.6 | 6.1 | 7.4 |
| 5.8 | 5.8 | 6.2 | 7.5 |
| 6.0 | 6.0 | 6.4 | 7.7 |
| 6.2 | 6.2 | 6.5 | 7.8 |
| 6.4 | 6.4 | 6.6 | 7.7 |
| 6.6 | 6.6 | 6.8 | 7.3 |
| 6.8 | 6.8 | 6.9 | 7.6 |
| 7.0 | 7.0 | 7.0 | 7.9 |
| 7.2 | 7.2 | 7.2 | 7.9 |
| 7.4 | 7.4 | 7.8 | 8.1 |

We claim:

1. A method for production of tetanus toxin, the method comprising steps of:
   providing a fermentation medium that is substantially free of animal-derived products and that comprises a protein product derived from a vegetable,
   culturing an organism of the species *Clostridium tetani* in the fermentation medium under conditions that allow production of tetanus toxin, and
   recovering tetanus toxin.

2. The method of claim 1, wherein in the step of providing a fermentation medium, the medium comprises the protein product derived from soybeans.

3. The method of claim 1, wherein in the step of providing a fermentation medium, the medium comprises hydrolyzed soy.

4. The method of claim 1, wherein in the step of providing a fermentation medium, the medium comprises hydrolyzed soy at a concentration between 10–300 g/L.

5. The method of claim 1, wherein in the step of providing a fermentation medium, the medium comprises hydrolyzed soy at a concentration of approximately 35 g/L.

6. The method of claim 1, wherein in the step of culturing, the culturing is performed until cell density of the culture decreases due to cell lysis.

7. The method of claim 1, wherein in the step of culturing, the culturing is performed until at least 48 hours after initial drop in cell density due to cell lysis.

8. A method for production of tetanus toxin, the method comprising steps of:
   providing a seed medium that is substantially free of animal-derived products and that comprises a protein product derived from a vegetable,
   culturing an organism of the species *Clostridium tetani* in the seed medium under conditions that allow growth of said organism to produce a cultured seed medium,
   providing a fermentation medium that is substantially free of animal-derived products and that comprises a protein product derived from a vegetable,
   inoculating the fermentation medium with the cultured seed medium,
   culturing an organism of the species *Clostridium tetani* in said fermentation medium under conditions that allow production of tetanus toxin, and
   recovering tetanus toxin.

9. The method of claim 8, wherein in the step of providing a seed medium, the seed medium comprises the protein product soybeans,
   and wherein in the step of inoculating a fermentation medium, the fermentation medium comprises the protein product derived from soybeans.

10. The method of claim 8, wherein in the step of providing a seed medium, the seed medium comprises hydrolyzed soy,
    and wherein in the step of inoculating a fermentation medium, the fermentation medium comprises hydrolyzed soy.

11. The method of claim 8, wherein in the step of providing a seed medium, the seed medium comprises hydrolyzed soy at a concentration between approximately 25–200 g/L,
    and wherein in the step of inoculating a fermentation medium, the fermentation medium comprises hydrolyzed soy at a concentration between approximately 10–100 g/L.

12. The method of claim 8, wherein in the step of providing a seed medium, the seed medium comprises hydrolyzed soy at a concentration between approximately 50–150 g/L;
    and wherein in the step of inoculating a fermentation medium, the fermentation medium comprises hydrolyzed soy at a concentration between approximately 20–60 g/L.

13. The method of claim 8, wherein in the step of providing a seed medium, the seed medium comprises hydrolyzed soy at a concentration of approximately 100 g/L;
    and wherein in the step of inoculating a fermentation medium, the fermentation medium comprises hydrolyzed soy at a concentration of approximately 35 g/L.

14. The method of claim 8, wherein in the step of culturing an organism of the genus Clostridium in a seed medium, the conditions comprise a temperature of approximately 34 degrees Celsius, and further comprise no decrease in cell density during culturing,
    wherein in the step of inoculating a fermentation medium with a cultured seed medium, 2 to 4 percent of the cultured seed medium is used to inoculate the fermentation medium, and
    wherein in the step of culturing said organism in said fermentation medium, the conditions that allow growth comprise a temperature of approximately 34 degrees Celsius and further comprise culturing until cell density of the culture decreases due to cell lysis.

15. A composition comprising an organism of the species *Clostridium tetani* and a culture medium for producing tetanus toxin wherein the medium is substantially free of animal-derived products and comprises a protein product derived from a vegetable.

16. The composition of claim 15, wherein the composition comprises the protein product derived from soybeans.

17. The composition of claim 15, wherein the composition comprises hydrolyzed soy.

18. The composition of claim 15, wherein the composition includes hydrolyzed soy at a concentration between about 10–100 g/L.

19. The composition of claim 15, wherein the composition comprises hydrolyzed soy at a concentration of about 35 g/L.

20. The composition of claim 15, and wherein the medium includes hydrolyzed soy present at a concentration between about 20–200 g/L.

21. The composition of claim 15, wherein the medium includes hydrolyzed soy present at a concentration of about 100 g/L.

* * * * *